US012578786B1

(12) United States Patent
Ravindran et al.

(10) Patent No.: US 12,578,786 B1
(45) Date of Patent: **\*Mar. 17, 2026**

(54) CUSTOMIZING VIRTUAL AND AUGMENTED REALITY EXPERIENCES FOR NEURODEVELOPMENTAL THERAPIES AND EDUCATION

(71) Applicant: FLOREO, INC., Chevy Chase, MD (US)

(72) Inventors: Vijay Ravindran, Washington, DC (US); Ali Moeeny, Baltimore, MD (US); Sarah Bhandiwad, Bethesda, MD (US)

(73) Assignee: Floreo, Inc.

( * ) Notice: Subject to any disclaimer, the term of this patent is extended or adjusted under 35 U.S.C. 154(b) by 0 days.

This patent is subject to a terminal disclaimer.

(21) Appl. No.: 19/210,730

(22) Filed: May 16, 2025

Related U.S. Application Data

(63) Continuation of application No. 18/795,031, filed on Aug. 5, 2024, now Pat. No. 12,333,065, which is a continuation of application No. 16/594,248, filed on Oct. 7, 2019, now abandoned.

(60) Provisional application No. 62/742,648, filed on Oct. 8, 2018.

(51) Int. Cl.

| | |
|---|---|
| *G06F 3/01* | (2006.01) |
| *G06T 19/00* | (2011.01) |
| *G09B 5/06* | (2006.01) |
| *G16H 20/70* | (2018.01) |

(52) U.S. Cl.
CPC ............ *G06F 3/011* (2013.01); *G06T 19/006* (2013.01); *G09B 5/06* (2013.01); *G16H 20/70* (2018.01)

(58) Field of Classification Search
CPC ....... G06F 3/011; G06T 19/006; G16H 20/70; G09B 5/06
See application file for complete search history.

(56) References Cited

U.S. PATENT DOCUMENTS

| | | | |
|---|---|---|---|
| 5,727,950 | A | 3/1998 | Cook et al. |
| 5,754,738 | A | 5/1998 | Saucedo et al. |
| 5,879,163 | A | 3/1999 | Brown et al. |
| 6,162,189 | A | 12/2000 | Girone et al. |
| 6,496,208 | B1 | 12/2002 | Bernhardt et al. |
| 6,611,242 | B1 | 8/2003 | Hongo et al. |
| 7,650,349 | B2 | 1/2010 | Yeh et al. |
| 8,503,720 | B2 | 8/2013 | Shotton et al. |
| 8,682,756 | B1 | 3/2014 | Tifford et al. |
| 8,934,026 | B2 | 1/2015 | Tian et al. |

(Continued)

OTHER PUBLICATIONS

Co-pending U.S. Appl. No. 16/594,248, inventors Ravindran; Vijay et al., filed Oct. 7, 2019.

(Continued)

*Primary Examiner* — Muhammad N Edun
(74) *Attorney, Agent, or Firm* — Wilson Sonsini Goodrich & Rosati

(57) ABSTRACT

Provided are platforms, methods, and systems to customize virtual or augmented reality (collectively, XR) content for an individual or a group of individuals, such as to treat a user having a mental or neurodevelopmental disorder (e.g., autism), train or educate an individual (e.g., student) or a group of individuals, or otherwise attend to a special need of an individual or a group of individuals. A graphical user interface may be used to edit the XR content.

26 Claims, 9 Drawing Sheets

(56)        References Cited

U.S. PATENT DOCUMENTS

| | | | |
|---|---|---|---|
| 9,262,673 | B2 | 2/2016 | Shotton et al. |
| 9,354,709 | B1 | 5/2016 | Heller et al. |
| 9,462,262 | B1 | 10/2016 | Worley, III et al. |
| 9,581,819 | B1 | 2/2017 | Boggs et al. |
| 9,652,031 | B1 | 5/2017 | Savastinuk et al. |
| 9,995,936 | B1 | 6/2018 | Macannuco et al. |
| 9,996,535 | B1 | 6/2018 | Skidmore et al. |
| 10,168,782 | B1 | 1/2019 | Tchon et al. |
| 10,186,168 | B2 | 1/2019 | Gobert et al. |
| 10,205,643 | B2 | 2/2019 | Fletcher et al. |
| 10,311,645 | B1 | 6/2019 | Ravindran et al. |
| 10,353,483 | B2 | 7/2019 | Kramer et al. |
| 10,417,704 | B2 | 9/2019 | Searson et al. |
| 10,467,234 | B2 | 11/2019 | Nerurkar et al. |
| 10,467,980 | B2 | 11/2019 | Watson et al. |
| 10,529,140 | B1 | 1/2020 | Ravindran et al. |
| 10,541,054 | B2 | 1/2020 | Zalis et al. |
| 10,621,164 | B1 | 4/2020 | Kain |
| 10,664,133 | B1 | 5/2020 | Rowny et al. |
| 10,702,773 | B2 | 7/2020 | Davis |
| 10,768,605 | B2 | 9/2020 | Dalal et al. |
| 10,824,238 | B2 | 11/2020 | Kramer et al. |
| 10,831,286 | B1 | 11/2020 | Pepose et al. |
| 10,831,733 | B2 | 11/2020 | Gomez et al. |
| 10,846,603 | B2 | 11/2020 | Yamagami et al. |
| 10,884,525 | B1 | 1/2021 | Vonsik et al. |
| 10,885,719 | B1 | 1/2021 | Ravindran et al. |
| 11,079,888 | B1 | 8/2021 | Gray et al. |
| 11,210,968 | B2 | 12/2021 | Clevenger et al. |
| 11,262,885 | B1 | 3/2022 | Burckel |
| 11,295,511 | B1 | 4/2022 | Yosifov et al. |
| 11,615,712 | B2 | 3/2023 | Park et al. |
| 11,630,633 | B1 | 4/2023 | Macdougall |
| 12,333,065 | B1 | 6/2025 | Ravindran |
| 2001/0025304 | A1 | 9/2001 | Keith, Jr. |
| 2002/0091687 | A1 | 7/2002 | Eglington |
| 2002/0107959 | A1 | 8/2002 | Shteyn |
| 2002/0174088 | A1 | 11/2002 | Liu et al. |
| 2003/0140018 | A1 | 7/2003 | Epstein et al. |
| 2004/0109009 | A1 | 6/2004 | Yonezawa et al. |
| 2004/0172347 | A1 | 9/2004 | Barthel |
| 2004/0197750 | A1 | 10/2004 | Donaher et al. |
| 2005/0024388 | A1 | 2/2005 | Takemoto |
| 2005/0054381 | A1 | 3/2005 | Lee et al. |
| 2005/0118996 | A1 | 6/2005 | Lee et al. |
| 2005/0143138 | A1 | 6/2005 | Lee et al. |
| 2005/0156932 | A1 | 7/2005 | Vienneau et al. |
| 2006/0235548 | A1 | 10/2006 | Gaudette |
| 2007/0214136 | A1 | 9/2007 | MacLennan et al. |
| 2008/0235164 | A1 | 9/2008 | Tian et al. |
| 2008/0280276 | A1 | 11/2008 | Raber et al. |
| 2009/0031239 | A1 | 1/2009 | Coleran et al. |
| 2009/0271715 | A1 | 10/2009 | Tumuluri |
| 2010/0074141 | A1 | 3/2010 | Nguyen |
| 2010/0262598 | A1 | 10/2010 | Koyama et al. |
| 2010/0278384 | A1 | 11/2010 | Shotton et al. |
| 2011/0009241 | A1 | 1/2011 | Lane et al. |
| 2011/0210915 | A1 | 9/2011 | Shotton et al. |
| 2012/0142415 | A1 | 6/2012 | Lindsay |
| 2012/0172126 | A1 | 7/2012 | Padovani et al. |
| 2012/0212405 | A1 | 8/2012 | Newhouse et al. |
| 2012/0218306 | A1 | 8/2012 | Mcardle et al. |
| 2012/0236029 | A1 | 9/2012 | Newhouse et al. |
| 2012/0242656 | A1 | 9/2012 | Mcardle et al. |
| 2012/0242798 | A1 | 9/2012 | Mcardle et al. |
| 2012/0246223 | A1 | 9/2012 | Newhouse et al. |
| 2012/0323824 | A1 | 12/2012 | Gansner |
| 2013/0117280 | A1 | 5/2013 | Donaldson et al. |
| 2013/0127980 | A1 | 5/2013 | Haddick et al. |
| 2013/0169514 | A1 | 7/2013 | Edwards et al. |
| 2013/0222273 | A1 | 8/2013 | Tan |
| 2013/0251126 | A1 | 9/2013 | Hollander et al. |
| 2014/0002493 | A1 | 1/2014 | Mitchell et al. |
| 2014/0028712 | A1 | 1/2014 | Keating et al. |
| 2014/0071165 | A1 | 3/2014 | Tuchschmid et al. |
| 2014/0139551 | A1 | 5/2014 | McCulloch et al. |
| 2014/0143676 | A1 | 5/2014 | Tan |
| 2014/0143687 | A1 | 5/2014 | Tan et al. |
| 2014/0143735 | A1 | 5/2014 | Dahn |
| 2014/0149177 | A1 | 5/2014 | Frank et al. |
| 2014/0176603 | A1 | 6/2014 | Kumar et al. |
| 2014/0204118 | A1 | 7/2014 | Berry et al. |
| 2014/0223462 | A1 | 8/2014 | Aimone et al. |
| 2014/0240313 | A1 | 8/2014 | Varga |
| 2014/0310595 | A1 | 10/2014 | Acharya et al. |
| 2014/0335497 | A1 | 11/2014 | Gal et al. |
| 2014/0342333 | A1 | 11/2014 | Knoche et al. |
| 2015/0019569 | A1 | 1/2015 | Parker et al. |
| 2015/0081685 | A1 | 3/2015 | Ashenfelter et al. |
| 2015/0091780 | A1 | 4/2015 | Lyren |
| 2015/0097860 | A1 | 4/2015 | Alaniz et al. |
| 2015/0097863 | A1 | 4/2015 | Alaniz et al. |
| 2015/0097864 | A1 | 4/2015 | Alaniz et al. |
| 2015/0243085 | A1 | 8/2015 | Newhouse et al. |
| 2015/0260474 | A1 | 9/2015 | Rublowsky et al. |
| 2015/0278695 | A1 | 10/2015 | Shah |
| 2015/0310444 | A1 | 10/2015 | Chen et al. |
| 2016/0019808 | A1 | 1/2016 | Chavez et al. |
| 2016/0063209 | A1 | 3/2016 | Malaviya |
| 2016/0077547 | A1 | 3/2016 | Aimone et al. |
| 2016/0081597 | A1 | 3/2016 | Bhavaraju et al. |
| 2016/0127552 | A1 | 5/2016 | Sharma et al. |
| 2016/0148417 | A1 | 5/2016 | Kim et al. |
| 2016/0196765 | A1 | 7/2016 | Stauch et al. |
| 2016/0249989 | A1 | 9/2016 | Devam et al. |
| 2016/0253843 | A1 | 9/2016 | Lee |
| 2016/0269631 | A1 | 9/2016 | Jiang et al. |
| 2016/0291922 | A1 | 10/2016 | Montgomerie et al. |
| 2016/0321414 | A1 | 11/2016 | Salganicoff et al. |
| 2016/0349838 | A1 | 12/2016 | Solomon et al. |
| 2016/0350595 | A1 | 12/2016 | Solomin et al. |
| 2016/0367202 | A1 | 12/2016 | Carter et al. |
| 2016/0371051 | A1 | 12/2016 | Rowe et al. |
| 2017/0007351 | A1 | 1/2017 | Yu |
| 2017/0048033 | A1 | 2/2017 | Porat |
| 2017/0059871 | A1 | 3/2017 | Hashiba et al. |
| 2017/0060831 | A1 | 3/2017 | Smythe et al. |
| 2017/0076491 | A1 | 3/2017 | Jiang et al. |
| 2017/0193551 | A1 | 7/2017 | Santi |
| 2017/0212651 | A1 | 7/2017 | Courvoisier et al. |
| 2017/0227754 | A1 | 8/2017 | Huang |
| 2017/0293705 | A1 | 10/2017 | Van Der Velden et al. |
| 2017/0329856 | A1 | 11/2017 | Jiang et al. |
| 2017/0332303 | A1 | 11/2017 | Sunay et al. |
| 2017/0365101 | A1 | 12/2017 | Samec et al. |
| 2018/0059812 | A1 | 3/2018 | Inomata et al. |
| 2018/0062931 | A1 | 3/2018 | Joshi et al. |
| 2018/0090029 | A1 | 3/2018 | Fisher et al. |
| 2018/0098813 | A1 | 4/2018 | Nesichi et al. |
| 2018/0101391 | A1 | 4/2018 | Cunha et al. |
| 2018/0121622 | A1 | 5/2018 | Armstrong et al. |
| 2018/0137771 | A1 | 5/2018 | Wahidy et al. |
| 2018/0173323 | A1 | 6/2018 | Harvey et al. |
| 2018/0174256 | A1 | 6/2018 | Franz et al. |
| 2018/0189568 | A1 | 7/2018 | Powderly et al. |
| 2018/0193589 | A1 | 7/2018 | McLaughlin et al. |
| 2018/0224928 | A1 | 8/2018 | Ross et al. |
| 2018/0247023 | A1 | 8/2018 | Divine et al. |
| 2018/0254097 | A1 | 9/2018 | Gani et al. |
| 2018/0293802 | A1 | 10/2018 | Hendricks et al. |
| 2018/0307303 | A1 | 10/2018 | Powderly et al. |
| 2018/0308377 | A1 | 10/2018 | Pena-Rios et al. |
| 2018/0314322 | A1 | 11/2018 | Tseng |
| 2018/0357915 | A1 | 12/2018 | Harlow et al. |
| 2018/0374268 | A1 | 12/2018 | Niles |
| 2019/0019092 | A1 | 1/2019 | Baughman et al. |
| 2019/0065027 | A1 | 2/2019 | Hauenstein et al. |
| 2019/0113973 | A1 | 4/2019 | Coleman et al. |
| 2019/0130781 | A1 | 5/2019 | Nissen et al. |
| 2019/0139426 | A1 | 5/2019 | Kesavadas et al. |
| 2019/0188450 | A1 | 6/2019 | Spivack et al. |
| 2019/0188876 | A1 | 6/2019 | Song et al. |
| 2019/0196663 | A1 | 6/2019 | Monastyrshyn et al. |
| 2019/0197141 | A1 | 6/2019 | Gomez et al. |

(56) References Cited

U.S. PATENT DOCUMENTS

| | | |
|---|---|---|
| 2019/0197785 A1 | 6/2019 | Tate-Gans et al. |
| 2019/0228533 A1 | 7/2019 | Giurgica-Tiron et al. |
| 2019/0232500 A1 | 8/2019 | Bennett et al. |
| 2019/0251965 A1 | 8/2019 | Dharne |
| 2019/0251966 A1 | 8/2019 | Dharne |
| 2019/0255350 A1 | 8/2019 | Malchano et al. |
| 2019/0279746 A1 | 9/2019 | Kohle et al. |
| 2019/0282324 A1 | 9/2019 | Freeman et al. |
| 2019/0285867 A1 | 9/2019 | Huang |
| 2019/0304188 A1 | 10/2019 | Bridgeman et al. |
| 2019/0318421 A1 | 10/2019 | Lyonnet et al. |
| 2019/0362312 A1 | 11/2019 | Platt et al. |
| 2019/0362557 A1 | 11/2019 | Lacey et al. |
| 2019/0362641 A1 | 11/2019 | Sukhwani et al. |
| 2019/0369838 A1 | 12/2019 | Josephson et al. |
| 2019/0380792 A1 | 12/2019 | Poltaretskyi et al. |
| 2020/0026922 A1 | 1/2020 | Pekelny et al. |
| 2020/0050342 A1 | 2/2020 | Lee |
| 2020/0051448 A1 | 2/2020 | Welch et al. |
| 2020/0065396 A1 | 2/2020 | Ozcaglar et al. |
| 2020/0066049 A1 | 2/2020 | Sun et al. |
| 2020/0073482 A1 | 3/2020 | Levesque |
| 2020/0090542 A1* | 3/2020 | Clevenger .............. G09B 5/065 |
| 2020/0092094 A1 | 3/2020 | Resch et al. |
| 2020/0111255 A1 | 4/2020 | Brodsky et al. |
| 2020/0111376 A1 | 4/2020 | Breeding et al. |
| 2020/0134780 A1 | 4/2020 | Chapiro et al. |
| 2020/0213117 A1 | 7/2020 | Resch et al. |
| 2020/0265754 A1 | 8/2020 | Buras et al. |
| 2020/0286294 A1 | 9/2020 | Musara |
| 2020/0289937 A1 | 9/2020 | Osman |
| 2020/0294408 A1 | 9/2020 | Olivieri et al. |
| 2020/0306643 A1 | 10/2020 | Borovikov et al. |
| 2020/0319856 A1 | 10/2020 | Loria |
| 2020/0320794 A1 | 10/2020 | Huang et al. |
| 2020/0327378 A1 | 10/2020 | Smith et al. |
| 2020/0327816 A1 | 10/2020 | Verma et al. |
| 2020/0334463 A1 | 10/2020 | Shapira |
| 2020/0337625 A1 | 10/2020 | Aimone et al. |
| 2020/0356897 A1 | 11/2020 | Diggle et al. |
| 2020/0388077 A1 | 12/2020 | Ninan et al. |
| 2020/0411199 A1 | 12/2020 | Shrager et al. |
| 2021/0011606 A1 | 1/2021 | Brown, IV et al. |
| 2021/0029803 A1 | 1/2021 | Olaleye et al. |
| 2021/0065573 A1 | 3/2021 | Rakshit et al. |
| 2021/0069574 A1 | 3/2021 | O'Dowd et al. |
| 2021/0089117 A1 | 3/2021 | Bodolec et al. |
| 2021/0090449 A1 | 3/2021 | Smith et al. |
| 2021/0097776 A1 | 4/2021 | Faulkner et al. |
| 2021/0133509 A1 | 5/2021 | Wall et al. |
| 2021/0191600 A1 | 6/2021 | Lemay et al. |
| 2021/0240279 A1 | 8/2021 | Harviainen et al. |
| 2021/0255730 A1 | 8/2021 | Gray et al. |
| 2021/0256874 A1 | 8/2021 | Harel et al. |
| 2021/0335490 A1 | 10/2021 | Arroyo Camejo et al. |
| 2021/0337341 A1 | 10/2021 | Sakuma |
| 2021/0346805 A1 | 11/2021 | Daniali |
| 2021/0369080 A1 | 12/2021 | Takahashi et al. |
| 2021/0369394 A1 | 12/2021 | Braido et al. |
| 2021/0383912 A1 | 12/2021 | Jackson et al. |
| 2021/0405738 A1 | 12/2021 | Bodolec et al. |
| 2022/0124143 A1 | 4/2022 | Rafkind et al. |
| 2022/0172633 A1 | 6/2022 | Jha et al. |
| 2022/0179552 A1 | 6/2022 | Burckel |
| 2022/0208016 A1 | 6/2022 | Le Chevalier |
| 2022/0229535 A1 | 7/2022 | Evangelista et al. |
| 2022/0255974 A1 | 8/2022 | Berliner et al. |
| 2022/0255995 A1 | 8/2022 | Berliner et al. |
| 2022/0304604 A1 | 9/2022 | Costea |
| 2022/0317830 A1 | 10/2022 | Skuratowicz et al. |
| 2022/0343590 A1 | 10/2022 | Jutan et al. |
| 2022/0343591 A1 | 10/2022 | Jutan et al. |
| 2023/0007085 A1 | 1/2023 | Berliner et al. |
| 2023/0100610 A1 | 3/2023 | Pastrana Vicente et al. |
| 2023/0105621 A1 | 4/2023 | Karri et al. |
| 2023/0129708 A1 | 4/2023 | Stone et al. |
| 2023/0164202 A1 | 5/2023 | Kumar Agrawal et al. |
| 2024/0081706 A1* | 3/2024 | Alailima .............. A61B 5/7455 |

OTHER PUBLICATIONS

Co-pending U.S. Appl. No. 17/110,383, inventors Ravindran; Vijay et al., filed Dec. 3, 2020.
Escobedo et al. Using Augmented Reality to Help Children with Autism Stay Focused. IEEE Pervasive Computing. Published: Feb. 28, 2014. pp. 38-46.
U.S. Appl. No. 15/782,216 Notice of Allowance dated Feb. 27, 2019.
U.S. Appl. No. 15/782,216 Office Action dated Feb. 8, 2019.
U.S. Appl. No. 15/782,216 Office Action dated Oct. 3, 2018.
U.S. Appl. No. 16/387,885 Notice of Allowance dated Sep. 25, 2019.
U.S. Appl. No. 16/594,248 Office Action dated Dec. 9, 2020.
U.S. Appl. No. 16/594,248 Office Action dated Feb. 5, 2024.
U.S. Appl. No. 16/594,248 Office Action dated Jan. 10, 2022.
U.S. Appl. No. 16/594,248 Office Action dated Jun. 12, 2023.
U.S. Appl. No. 16/594,248 Office Action dated Jun. 21, 2021.
U.S. Appl. No. 16/594,248 Office Action dated Oct. 7, 2022.
U.S. Appl. No. 16/697,816 Notice of Allowance dated Sep. 23, 2020.
U.S. Appl. No. 16/697,816 Office Action dated May 26, 2020.
U.S. Appl. No. 18/795,031 Notice of Allowance dated Feb. 18, 2025.
U.S. Appl. No. 18/795,031 Office Action dated Sep. 27, 2024.

* cited by examiner

200

602

604

606

602

620

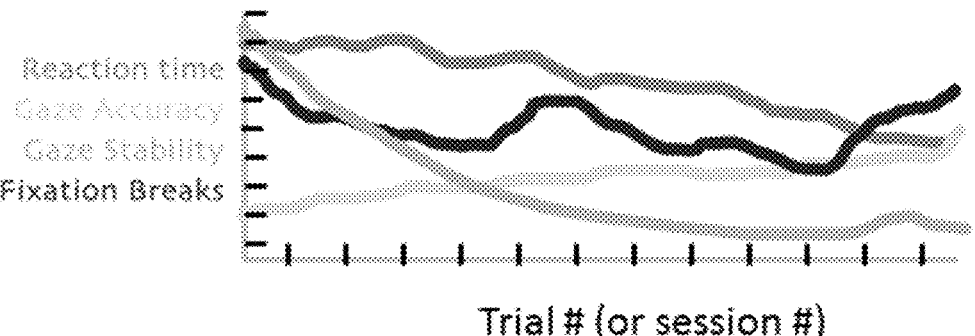

Progress report

| | | |
|---|---|---|
| Task | Find the animal | Sensory Integration Category |
| Started | July 20, 2016 | Age 37 yrs |
| Total Sessions | 132 | 18 left out of 150 Recommended Total |
| Total minutes | 1549 | Exceeds 10 minutes per session effective session duration |
| Total Trials | 2187 | Meets minimum effective repetitions per session |
| Successes | 1751 | |
| Success Rate | 80% | Exceeds expected 75% success rate |
| Best Week | 96% | |

Reaction time
Gaze Accuracy
Gaze Stability
Fixation Breaks

Trial # (or session #)

*FIG. 7*

CUSTOMIZING VIRTUAL AND AUGMENTED REALITY EXPERIENCES FOR NEURODEVELOPMENTAL THERAPIES AND EDUCATION

CROSS-REFERENCE TO RELATED APPLICATIONS

This application is a continuation of U.S. patent application Ser. No. 18/795,031, filed Aug. 5, 2024, which is a continuation of U.S. patent application Ser. No. 16/594,248, filed Oct. 7, 2019, which claims the priority benefit to U.S. Provisional Application No. 62/742,648, filed on Oct. 8, 2018; the entire contents of which are incorporated herein by reference for all purposes.

BACKGROUND

Virtual or augmented reality is the coordinated experience of a user in or with an environment manufactured by, and housed in, computer processors and memory, where the environment is coordinated with the user's motion and use of the senses such as sight, sound, and touch. Augmented reality systems may be used to augment, emphasize, or otherwise modify the perception both of real-world objects and completely virtual objects. Virtual or augmented reality systems may be used to create experiences so that a user may encounter, learn, or train while being exposed to little or no physical risk. For example, virtual or augmented reality systems may be used for neurodevelopmental therapies for disorders such as autism or education.

Autism, also known as autism spectrum disorder (ASD), refers to a group of complex neurodevelopmental disorders in which affected individuals commonly show difficulties understanding and engaging in social interactions and communication and often exhibit repetitive behaviors. Autism affects at least 1% of the US population, and is becoming more prevalent in the population every year. Although there is no known cure, today, autism therapy ranges across a myriad of specialties including neurology, psychiatry, physical therapy, occupational therapy, behavioral therapy, and speech language pathology. Such therapeutic methods can help autistic individuals gain social and communication skills.

SUMMARY

It is often the case that different users of a virtual or augmented reality (collectively, XR) system are provided with the same limited selection of XR environments. However, particularly for learning or training applications, such as when XR is used for neurodevelopmental therapies or for students seeking the aid of XR systems to learn or improve a skill set, such limited selection may not accurately, or sufficiently, address the individual characteristics, problems, and/or learning profiles of the different users. For instance, some users may be more responsive to audio stimulation than visual stimulation or to a first selection of colors than a second selection of colors. In another example, some users may have a first education level (e.g., with a more advanced set of vocabulary or social training) than some users having a second education level (e.g., with a more elementary set of vocabulary or social training). In another instance, some users may speak different languages or come from different cultural geographic backgrounds. As a result, a particular design of a particular XR environment may not be readily compatible with, or as efficient with, all users. Thus, recognized herein is the need for platforms, methods, and systems for the flexible customization of XR experiences for the treatment and/or education of individual users. Beneficially, the platforms, methods, and systems may customize XR content for an individual or a group of individuals, such as to treat a user having a mental or neurodevelopmental disorder (e.g., autism), train or educate an individual (e.g., student) or a group of individuals, or otherwise attend to a special need or preferences of an individual or a group of individuals.

The present disclosure may employ methods for creating, editing, and/or using a virtual world that provides visual, auditory, and/or haptic stimulation and experiences. In some instances, the methods may include creating, editing, and/or using a template XR experience or a library of templates. In some instances, the methods may include profiling one or more users and using the results of such profiling to create, edit, and/or use the virtual world. In some instances, the methods may include monitoring the user's interaction with the virtual and real world, measuring the user's progress toward one or more therapeutic or educational goals, and editing the virtual world based on such monitored results to improve the efficiency or accuracy of the XR experience. The present disclosure may employ platforms having graphical user interfaces (GUIs) for inputting user instructions for the creation, editing, and/or use of virtual world content. In some instances, the GUIs may output an intermediate and/or final result of the user instructions to aid in the creation, editing, and/or use of the virtual world content.

The virtual or augmented reality system of the present disclosure can comprise a display screen for visual engagement, headphones or speakers for auditory stimulation, and controllers for physical input as well as haptic feedback. The method may further comprise the user interacting with the virtual world using eye movement, head movement, and/or one or more controllers attached to a body and/or limb of the user. One or more sensors integrated or external to the virtual or augmented reality system may detect the user's interactions with the virtual world. Monitoring may be in real-time.

The platforms, methods, and systems of the present disclosure may be used for treating or supplementing the treatment of a user for a mental or neurodevelopmental disorder, such as autism, using a virtual or augmented reality system. The platforms, methods, and systems of the present disclosure may be used for educating or training, or supplementing the education or training, of a user, such as a student, using a virtual or augmented reality system.

The method may further comprise the user interacting with a therapist, parent, or peer to progress toward the one or more therapeutic or educational goals. For example, the user may be paired with the therapist, parent, teacher, peer, or a plurality of therapists, parents, teachers, or peers, or any combination of the above. In some instances, a paired individual or entity may be capable of influencing the user's experience in the virtual world, such as by creating, modifying, and/or removing the visual, auditory, and/or haptic stimulations provided to the user in the virtual world.

In some instances, the virtual or augmented reality experiences and therapies can be tailored to the needs of individual users either manually by a human expert (e.g., therapist, educators, etc.) or using computer algorithms or artificial intelligence. For example, the tailoring can be performed based at least on prior conditions and/or other assessments of the user and/or based on data collected throughout the user's and/or others' use of the system.

The platforms, methods, and systems of the present disclosure may be used by domain experts (e.g., teachers, educators, therapists, parents, etc.) to create new supervised interactive XR content. The interactive XR content may be published on the platform to be available for a target audience. For example, the target audience may be a specified user, group of users, groups of users, or the public. The creators and/or publishers of the interactive XR may interface with the platform with minimal technical understanding or expertise in the authoring, playback or publication infrastructure.

The platforms, methods, and systems of the present disclosure may be used to review the XR content created from a clinical efficacy perspective, safety perspective, publication rights perspective, or other perspectives before permitting distribution of the content to a wider user base.

The platforms, methods, and systems of the present disclosure may provide for the authoring, editing, collaborative contribution, review, and/or troubleshooting (e.g., debugging) of the supervised interactive XR content.

The platforms, methods, and systems of the present disclosure allow for a separation of XR content definitions that enables publication of new content without the need for conventional updates through the underlying operating system or distributor (e.g., app store).

The platforms, methods, and systems of the present disclosure may be used to publish XR content authored or modified for individual users in a clinical context, akin to the prescription of individualized regimens. Therapeutic or training regimens may be monitored and adjusted based on the progress of users by manual intervention of domain experts and/or by algorithms. For example, one or more processors may be programmed to execute one or more algorithms to adjust the XR content (e.g., a parameter, a duration, etc.) or prescription thereof with respect to the monitored user. Such monitoring and adjustment may be made without technical expertise in the platform or infrastructure.

The platforms, methods, and systems of the present disclosure may be used to test play or experiment with new content or modifications to existing content for research or development purposes.

In some instances, different virtual or augmented reality experience may be organized in a library and be available for prescription or recommendation by the human expert or computer algorithms (e.g., artificial agent) to caregivers, parents, or the users themselves.

In an aspect, provided is a platform for editing virtual or augmented reality content, comprising: (a) a user interface comprising an editable network of nodes and connectors representing a sequence of logical flow paths in a virtual or augmented reality experience, wherein a node is associated with a state of an asset in the virtual or augmented reality experience, and a connector between two nodes defines a chronological sequence between two states of the respective two nodes in the virtual or augmented reality experience; and (b) an interactive control module configured to define a first node, wherein the interactive control module is presented upon selection of the first node from the editable network of nodes in the user interface.

In some embodiments, the state of the asset in the virtual or augmented reality experience is configured to provide visual, auditory, or haptic stimulation to a user of the virtual or augmented reality experience.

In some embodiments, the asset comprises a plurality of states and a plurality of transitions associated between different states of the plurality of states, wherein the state of the asset represents an instance of the asset in the virtual or augmented reality experience.

In some embodiments, the asset is defined by one or more data files selected from the group consisting of a model file, an audio file, a video file, an image file, an animation controller file, a mesh file, an object template file, and an animation file.

In some embodiments, the sequence of logical flow paths in the virtual or augmented reality experience is configured to direct a user of the virtual or augmented reality experience to achieve one or more therapeutic or educational goals.

In some embodiments, the interactive control module is configured to define a first state of a first asset associated with the first node. In some embodiments, the interactive control module is configured to replace the first state of the first asset associated with the first node with a second state of the first asset. In some embodiments, the interactive control module is configured to delete the first state of the first asset associated with the first node.

In some embodiments, the first node is a conditional node connected to a second node, wherein the second node is connected to a plurality of different conditional nodes including the first node, wherein the plurality of different conditional nodes are each associated with a condition.

In another aspect, provided is a method for editing virtual or augmented reality content, comprising: (a) providing a user interface comprising an editable network of nodes and connectors representing a sequence of logical flow paths in a virtual or augmented reality experience, wherein a node is associated with a state of an asset in the virtual or augmented reality experience, and a connector between two nodes defines a chronological sequence between two states of the respective two nodes in the virtual or augmented reality experience; and (b) editing the editable network of nodes and connectors by adding a node to the editable network, removing a node form the editable network, modifying a connectivity between a plurality of nodes in the editable network, changing a definition of a node in the editable network of nodes, or a combination of the above.

In some embodiments, the method further comprises publishing the editable network of nodes or one or more nodes of the editable network to a library accessible by a plurality of different users.

In some embodiments, the method further comprises further editing the editable network of nodes published in the library to generate an edited network of nodes.

In some embodiments, the method further comprises publishing and distributing the edited network of nodes.

In some embodiments, the method further comprises prescribing or assigning the virtual or augmented reality experience to a target user, target group of users, or target groups of users.

In some embodiments, the state of the asset in the virtual or augmented reality experience is configured to provide visual, auditory, or haptic stimulation to a user of the virtual or augmented reality experience.

In some embodiments, the sequence of logical flow paths in the virtual or augmented reality experience is configured to direct a user of the virtual or augmented reality experience to achieve one or more therapeutic or educational goals.

In some embodiments, the asset comprises a plurality of states and a plurality of transitions associated between different states of the plurality of states, wherein the state of the asset represents an instance of the asset in the virtual or augmented reality experience.

In some embodiments, the asset is defined by one or more data files selected from the group consisting of a model file, an audio file, a video file, an image file, an animation controller file, a mesh file, an object template file, and an animation file.

In some embodiments, the editing in (b) comprises replacing a first state of a first asset associated with the node with a second state of the first asset.

In some embodiments, the editing in (b) comprises deleting a first state of a first asset associated with the node.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 7 shows an illustration of a progress report generated from a user's response to an augmented reality or virtual reality experience.

DETAILED DESCRIPTION

Figure 1:
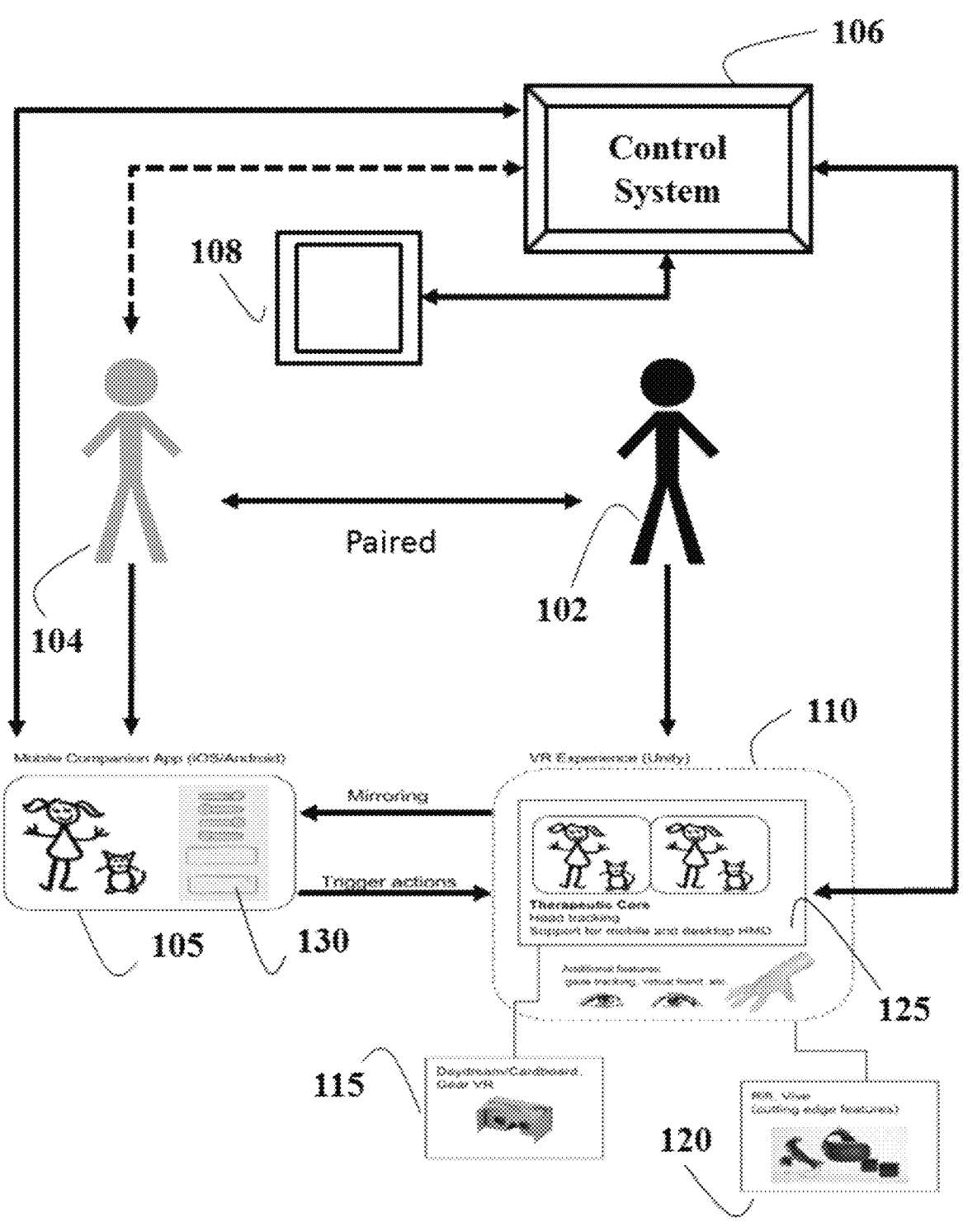
FIG. 1 shows a schematic illustration of a virtual or augmented reality system.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Virtual Reality (VR) or Augmented Reality (AR) Systems

In an aspect, provided are platforms, systems, and methods for providing a user with a XR experience. This may comprise designing, creating, modifying, and/or selecting the appropriate virtual or augmented world for the user. Such designing, creating, modifying, and/or selecting can be performed by assessing and/or profiling the user and pairing the user with one or more goals. For example, a goal can be a therapeutic goal and/or an educational goal. The XR experience provided to the user can be associated with the one or more goals paired with the user, designed to help the user achieve or progress towards the one or more goals. In some cases, each user may be uniquely profiled prior to, during, or subsequent to the user's XR experience. In some cases, each user may be categorized into a type of pre-existing user profile, such as from a library of user profiles. In some cases, a XR experience may be created for each user or each type of user. In some cases, a XR experience template may be created for a type of user profile. For example, a XR experience template may be selected from a pre-existing library of XR experience templates. The library of templates may be updated with new templates or templates modified or otherwise refined based on new users and/or uses of the existing templates.

In some instances, the XR experiences can be designed, created, modified, and/or selected manually by a human domain expert (e.g., therapist, educators, teachers, parents, etc.) and/or using computer algorithms or artificial intelligence. For example, the designing, creating, modifying, and/or selecting can be performed based at least in part on prior conditions and/or other assessments of the user and/or based on data collected throughout the user's and/or others' use of the system. The human expert or computer algorithms may recommend or prescribe different virtual or augmented reality experiences by selecting from the library of XR experience templates, creating a new XR experience, and/or modifying an existing XR experience template for the user. The prescription or recommendation of a new or existing XR experience may be provided to caregivers of the users, parents of the users, the users themselves, or other individuals or entities (e.g., schools, hospitals, etc.) affiliated with the users.

In the virtual or augmented world, the user can be presented with visual, auditory, and/or haptic stimulation. The user's interactions with the virtual, augmented, and/or real world can be monitored, and the user's progress towards one or more goals can be measured. For example, the user's interactions, reactions, and/or responses to the stimulations presented in the virtual world can be quantified based at least in part on sensory data measured for the user, such as a reaction time, gaze accuracy, gaze stability, response volume, and/or other forms or units of outputs by the user. In some cases, the user's progress toward one or more goals can be quantified based at least in part on such quantifications. In some cases, the user's progress toward one or more goals can also be measured based on qualitative observations made by another user monitoring the user's interactions, reactions, and responses in the virtual world, such as a therapist, educator, operator, or supervisor. For example, the user's progress toward one or more goals can be measured based on subjective and/or objective feedback from the monitoring user. In some instances, the user's progress toward one or more goals can be measured by comparing the user's performance in an evaluation, whether in or outside of the XR experience, prior to and subsequent to the user's XR experience. In some cases, the platforms, systems, and methods may further include editing or otherwise modifying a XR content to improve the potency, efficiency, or accuracy of the XR experience, such as based on the user's current or prior performance with the XR content.

The present disclosure may employ platforms having graphical user interfaces (GUIs) for inputting user instructions for the designing, creating, modifying, selecting, and/or use of virtual or augmented reality content. In some instances, the GUIs may output an intermediate and/or final result of the user instructions to aid in the creation, editing, and/or use of the virtual or augmented world content. In some instances, one or more parameters and/or stimulations in a virtual world can be provided or adjusted in real-time, such as by another user (e.g., therapist, educator, operator, supervisor) monitoring the user in the virtual or augmented world, for example, based on the user's interactions, reactions, or responses (or lack thereof) to a previous stimulation.

The virtual or augmented reality system may be a virtual reality system in which the user is presented with content in an environment that may be separate from the surrounding of the user. Alternatively, the virtual or augmented reality system may be an augmented reality system in which the user is presented with content that may be overlaid or at least partially integrated with the environment of the user.

Such system can comprise a display for presenting the user with content. Such display can be provided to the user through a user device (e.g., mobile device, computer, tablet, laptop, etc.), for instance. The user device may or may not be portable. Visual stimulation may be provided by presenting one or more images or video on a display screen. The system can further comprise one or more headphones, earphones, or speakers for providing auditory stimulation by presenting the user with audio. The one or more headphones, earphones, or speakers may be synchronized with images or video provided by the display screen to the user. In some instances, the user may access the virtual or augmented reality system with the use of a supplemental headgear (e.g., Google® Daydream/Cardboard, Oculus® Gear/Rift, and HTC® Vive). The system can further comprise one or more controllers for presenting the user with haptic stimulation. The controllers can be configured to, for example, vibrate. The controllers can comprise an actuator. The controllers may be attached (or otherwise coupled) to one or more body parts (e.g., limbs) of the user. The display can receive the one or more images or video, the headphone, earphone, or speaker can receive the audio, and the controllers can receive the haptic output to present to the user through a computer control system.

The user may interact with the virtual or augmented world using eye movement, head movement, or one or more controllers attached to the body and/or the limb of the user. To track the user's movement, the system may employ one or more sensors, including one or more cameras. A camera may be a charge coupled device (CCD) camera. The camera may record a still image or video. The image or video may be a two-dimensional image or video or a three-dimensional image or video. The system may employ other optical sensors, auditory sensors (e.g., microphones), touchpads, touchscreens, motion sensors, heat sensors, inertial sensors, touch sensors, or other sensors. The one or more sensors may be capable of measuring sensory data indicative of an output by a user (e.g., eye movement, head movement, facial expressions, speech, etc.) or lack thereof. The user may be tracked or monitored in real-time using the sensors. The monitoring may or may not be remote. The monitoring may be over one or more networks.

The method may further comprise the user interacting with one or more other individuals to progress toward the one or more goals. For example, the user may be paired with an operator, therapist, educator, parent, peer, or a plurality of operators, therapists, educators, parents, or peers, or any combination of the above. In some instances, a paired individual or entity may be capable of influencing the user's experience in the virtual or augmented world, such as by creating, modifying, and/or removing the visual, auditory, and/or haptic stimulations provided to the user in the virtual or augmented world. In some instances, the user may interact with a paired individual in the virtual or augmented world (e.g., as avatars). In some instances, the paired individual may monitor the user without influencing or otherwise interacting with the user in the virtual or augmented world. The paired individual can be located remotely from the user. The paired individual may or may not be the individual responsible for designing, creating, modifying, and/or selecting the XR experience for the user.

Beneficially, the platforms, methods, and systems described herein may flexibly customize XR content for an individual or a group of individuals, such as to treat a user having a mental or neurodevelopmental disorder (e.g., autism), train or educate an individual (e.g., student) or a group of individuals, or otherwise attend to a special need of an individual or a group of individuals. Further, the platforms, methods, and systems described herein may customize XR content for a specific goal, such as a therapeutic goal (e.g., learn or train a certain social sill, etc.) and/or an educational goal (e.g., learn the alphabet, improve mathematical skill, etc.).

The XR systems described herein may further provide a low cost, accessible therapeutic solution for users. Alternatively or in addition, the XR systems described herein may provide educational and/or entertainment value to users. User may or may not have a mental or developmental disorder.

For example, the platforms, methods, and systems of the present disclosure may be used for treating or supplementing the treatment of a user for a mental or neurodevelopmental disorder, such as autism, attention deficit hyperactivity disorder (ADHD), and social anxiety disorder, using a virtual or augmented reality system. In another example, the platforms, methods, and systems of the present disclosure may be used for educating or training, or supplementing the education or training, of a user, such as a student, using a virtual or augmented reality system.

In some cases, users who can benefit from these methods can be divided into characteristic groups, or in some cases, distinct types of user profiles. One group, or type of user profile, may comprise individuals with cognitive or perceptual conditions that need a more gentle and controlled introduction to certain aspects of the real world. These cognitive or perceptual conditions may include mental conditions such as a variety of phobias (e.g., arachnophobia, agoraphobia, acrophobia, social phobia and anxiety disorder), disorders involving distortions in the perception of one's own body (e.g., anorexia nervosa), and any mental or neurological condition that can cause sensory overload (e.g., ADHD). One group, or type of user profile, may comprise individuals who have conditions that prevent them from acquiring, or make it difficult for them to acquire, skills (e.g., social skills) through the normal course of development or the natural course of recovery from a trauma or disease. This may include individuals with autism, individuals with social (pragmatic) communication disorder, as well as those individuals that require language therapy, occupational therapy, behavioral therapy or physical therapy. One group, or type of user profile, may comprise a diverse group of individuals that can benefit from novel intervention methods that were not possible outside of virtual reality (VR) or augmented reality (AR). This group may include individuals diagnosed with conditions that can improve by having the individual observe and involve oneself in conversation in a virtual world to improve self-compassion or self-esteem (the lack of which are both symptoms of clinical depression). The group may also include any and all individuals in the general population that may benefit from practicing social skills or routines in a controlled environment.

Users can also be categorized into other types of groups, or distinct types of user profiles, based on other factors, such as gender (e.g., male, female, unidentified, etc.), age (e.g., 10, <10, >20, etc.), educational level (e.g., elementary school level, $3^{rd}$ grade, $4^{th}$ grade, middle school level, high school diploma, bachelors and above, doctorate level, etc.), type of disorder, prior exposure to XR therapies (e.g., yes/no, less than 1 year experience, more than 3 years experience, etc.), and other factors. Beneficially, users in the different groups can be provided different types of XR experiences either selected from a pre-existing library of templates, or created and/or modified based on group characteristics and/or user characteristics.

Furthermore, the XR system may facilitate data collection during or subsequent to treatment. For example, a user's progress toward one or more goals may be measured with significantly higher accuracy and precision than traditional methods of therapy or education. The XR system may be capable of collecting data that was previously unavailable for measurements via traditional methods. For example, the XR system may comprise one or more integrated or external sensors that are capable of measuring sensory data indicative of an output by a user (e.g., eye movement, head movement, facial expressions, speech, etc.). The one or more sensors may be capable of measuring sensory data indicative of a user's progress toward one or more goals, such as a reaction time, gaze stability, gaze accuracy, response volume, the presence or lack of a movement, the presence or lack of speaking, or other outputs by the user. A user's progress toward achieving a goal (e.g., increasing ability to concentrate) may be quantified more accurately and precisely than traditional methods (e.g., that rely on manual observations of a user or of a video recording of a user). For example, the XR system may track a user's gaze with one or more integrated sensors that are much more accurate than manual observations that predict a direction of a gaze. Additionally, the integrated sensors in the XR system allow the measuring of a user's interactions, reactions, and responses to a situation without interrupting, or being exposed to, the user who is wholly immersed in a XR environment—for example, in contrast, traditionally, the user may become aware of the artificiality of a therapy or education session, such as via presence of another human or a camera, and change his or her behavior based on such awareness, resulting in biased or otherwise inaccurate results.

The systems and methods may allow a therapist or educator to prescribe or otherwise assign one or more XR sessions to achieve one or more goals to a user. The user may perform the prescribed sessions without direct supervision from the prescriber. In some instances, the sessions are capable of being reviewed at a later time and place. Alternatively or in addition, the sessions are capable of being monitored directly or indirectly (e.g., remotely) in real time.

The therapy sessions can be monitored by any other individual, such as a parent or guardian in real time or at a later time and place. As used herein, real time can include a response time of less than 1 second, tenths of a second, hundredths of a second, or a millisecond. Real time can include a process or operation (e.g., monitoring of an action by a user) occurring simultaneously or substantially simultaneously with another processor or operation (e.g., performing the action by the user).

In some cases, data collected (or recorded) for one or more users may be aggregated to build behavior models for one or more conditions (e.g., mental or developmental disorders). Such behavior models can be leveraged as diagnostic tools for users to be evaluated through the XR system. The behavior models can be used to profile a user and/or assign one or more goals (e.g., therapeutic, educational) to the user. For example, a plurality of behavior models for different mental or developmental disorders can be stored in a library of behavior models, such as in one or more databases. A behavior model for a first type of developmental disorder can comprise data exhibited by one or more users known to suffer from the first type of developmental disorder when placed in a first XR environment. When a user to be diagnosed is placed in the same first XR environment, or an environment similar to the first XR environment, the data collected on the user may be compared to the behavior model for the first type of developmental disorder to determine whether the user has the first type of developmental disorder or not, or a degree to which the user suffers from the first type of developmental disorder. In some instances, the data collected for the user to be diagnosed may be compared to a plurality of behavior models to determine which one or more conditions the user may suffer from (and to what degree). By way of example, the higher the % similarity between the collected data for the user and the data stored for the behavior model, the more likely it is (and with higher degree) that the user suffers from the condition of the behavior model.

In some instances, where users are students and the goals relate to educational goals, XR content can be keyed to traditional educational methods. As an example, the XR content may adopt a spaced learning method where the learning content is repeated three times, with two short breaks in between the repetition during which students are directed to perform other activities (e.g., physical activity). To parallel the spaced learning method, the XR content may direct a user through five environments, the first including a learning content, the second directing the student to perform an unrelated activity (e.g., a puzzle game), the third repeating the first, the fourth directing the student to perform another unrelated activity (e.g., a physical activity such as jumping), and the fifth again repeating the first. In another example, the XR content may adopt a flipped classroom learning method, and the XR content may direct a user to teach an avatar to perform an activity in which the user is supposed to be learning themselves.

In some instances, where users are subjects of neurodevelopmental disorders and the goals relate to therapeutic goals, XR content can be keyed to virtual behavioral intervention principles used by other traditional methods of therapy. For example, in some cases, naturalistic behavioral intervention techniques may be employed. Naturalistic therapy, or natural environment teaching ("NET"), may occur in the user's natural environment. Methods and systems herein can integrate some key attributes of NET interventions into XR therapy. In some examples, the system may provide the user with the opportunity to select a type of virtual reality or augmented reality content or a treatment program (e.g., selecting the type of virtual environment such as the 'zoo' or a 'train station') and encourage supervisors or other third parties monitoring the user ("supervisors") to follow established training manuals, such as the Hanen OWL guidelines which teach the Observe, Wait, and Listen technique. Under these guidelines, supervisors may let the user explore the virtual environment while observing carefully what interests the user, wait for the user to make spontaneous comments or actions, listen carefully to what the user says or signs, and plan the next steps of therapy based on these comments or signs. In some examples, the system may permit a user to create a communication or play opportunity, if needed. That is, if the user does not communicate or do anything, the system can use playful obstructions or a similar technique to create a communication or play opportunity. For instance, a user that stares at only one animal silently may begin to speak if the therapist avatar blocks the user's view of the animal, or, alternatively, the user may start a game of trying to get past the therapist. Once the user starts doing something, the therapy can return to the OWL guidelines. In some examples, the system can provide the user with prompts of varying supportiveness to complete a task if there is a specific task to complete. In some examples, the system can reward the user for succeeding in such tasks. Such reward may be, for example, an image, audio or video that is pleasing to the user, a pleasing stimulus, or a compliment from a third party (e.g., supervisor).

In doing so, the system may provide prompts of varying supportiveness throughout the process. For example, the prompts may include, in the order of least supportive to most supportive: lightweight prompts by the software (e.g., a clickable item that blinks or is slightly translucent or a virtual hand suggesting where a user can move certain blocks); leading comment by a supervisor or therapist (e.g., using suggestive phrases such as "I see something interesting" or "That animal looks hungry"); verbal instruction (e.g., telling the user directly what to do); imitative model (e.g., a therapist or supervisor in real life, or alternatively as an avatar in the virtual environment, demonstrating a desired action so that the user can imitate); and physical prompts (e.g., directing the user by using hand-over-hand support through a desired action, or moving the user's head in an intended direction). Incorporating such virtual NET-style intervention, the system can create and provide XR environments with varying levels of difficulty, in which the user always succeeds in a given task, with or without supportive prompts. Through adaptations of such key principles, the system may provide goal-oriented therapies, such as, for example, therapies which build social connections, therapies which teach stories, and sensory-based therapies.

In another example, the XR content may be tied to therapies that build social connections between the user and other individuals. The other individuals may include one or more users that are also under treatment. These therapies can include the training of developmental skills such as joint attention (e.g., eye contact), social reciprocity (e.g., taking turns), and pragmatic intentions (e.g., problem solving or communicating acceptance). For example, a therapy module for developing inferencing may help prepare the user to become capable of learning how to recognize and interpret facial expressions, and a therapy module for developing joint attention may help prepare the user to become capable of understanding other people's perspectives. In some aspects, the system may provide therapies which teach functional skills using stories. These therapies can include building a practice environment for both routine tasks such as crossing a street and non-routine tasks such as responding to fire alarms or participating in a Halloween trick-or-treating activity. Other practice environments include interacting with a police officer that a user meets in an urban street. Beneficially, such stories provide an effective and entertaining ('fun') solution to teach users how to navigate everyday interactions by placing the users in a controlled virtual or augmented reality environment, thereby shielding the users from potential actual harms and retaining control to effectively guide the users at a flexible pace.

In another example, the system may provide sensory-based therapies. Sensory-based therapies can include using a XR environment to build specific calming or stimulating experiences with a focus on helping users with neurodevelopmental disorders or disabilities, such as autism, to manage or respond to otherwise challenging environments and situations. For example, a calming module may allow a user to play a simple and delightful musical instrument using just the direction of his or her gaze.

Interacting with a XR Experience

The XR content may include a network or graph of interactions that are triggered either by one or more actions of the user or by a supervisor or other third party that is monitoring the user. In some instances, an interaction, reaction, or response may be triggered by a peer (e.g., another user user). Every discrete action from the user can trigger a combination of animation, audio, and/or visual instructions to the supervisor. A supervisor, who may or may not be a therapist or educator, can directly monitor and supervise the user receiving the XR therapy through the use of a companion application. Such monitoring may occur remotely, wherein the user and the supervisor are physically and geographically at a significant distance from each other (e.g., different buildings, different countries, etc.). Alternatively or in addition, such monitoring may occur as in-room monitoring. The platforms, systems, and methods may allow a user to edit the XR content, such as by modifying the network or graph of interactions. The platforms, systems, and methods may allow a user to edit the content of a companion application that is paired and used with the XR content.

The system can comprise at least one, at least two, or at least three devices: one device capable of providing a virtual reality or augmented reality environment (e.g., smartphone, dedicated headset device like an HTC® Vive, Google® Cardboard headset) to the user, a second device (or same device as the first device), capable of providing a companion application to the supervisor, and a third device (or same device as the first and/or second device), capable of providing a user interface for editing XR content. The at least three devices can be communicatively coupled together, such as via tangible connection cable or wireless or Bluetooth pairing. Through the companion application, a supervisor may access, and, if needed, intervene in, the user's virtual or augmented reality experience. As an alternative, the system can comprise a single integrated device.

FIG. 1 shows a schematic illustration of a virtual or augmented reality system. A user 102 may be paired with a supervisor 104. The user 102 may be a user of a XR experience 110. The user 102 may have a condition, such as a mental or developmental disorder (e.g., autism). Alternatively or in addition, the user 102 may be a student. The user 102 may access the XR experience 110 via a first user device (not shown). The first user device may be any device comprising one or more displays, such as a monitor, screen, mobile phone, computer, smartphone, laptop, tablet, television, smart television, or other device. For example, the user 102 may access the experience 110 through the use of supplemental headsets 115 and 120 (e.g., Google® Daydream/Cardboard, Oculus® Gear/Rift, HTC® Vive, etc.).

The first user device may be communicatively coupled to one or more sensors, such as described elsewhere herein. The one or more sensors may be integrated in the first user device or external to, and operatively coupled to, the first user device, such as via wired or wireless (e.g., Bluetooth, Wi-Fi, Near Field Communication (NFC), etc.) connections. The one or more sensors may be capable of collecting data on the user 102, such as the user's interactions, reactions, and/or responses to one or more components and/or stimulations in the XR experience 110.

The XR experience 110 may comprise one or more XR scenes 125. For example, the XR experience 110 may comprise a time-dependent progression of one or more XR scenes 125. The XR scenes 125 may be dynamic, such as comprising one or more dynamic components (e.g., animation, audio, etc.) and/or components that can be triggered to change. The user 102 may be capable of interacting with, or reacting to or responding to, one or more components of the XR scenes 125. The user 102 may have a stereoscopical view of the one or more XR scenes 125 in the XR experience 110. The XR experience 110 can be a 360° experience. The XR experience 110 may be capable of presenting one or more stimulations, such as visual stimulations, audio stimulations, and/or haptic stimulations, such as via the first user device. Alternatively or in addition, the one or more stimulations may be provided via one or more external devices operatively coupled to the first user device, such as via wired or wireless connections. Such other devices can include, for example, other displays, screens, speakers, headphones, earphones, controllers, actuators, lamps, or other devices capable of providing visual, audio, and/or haptic output to the user 102.

The supervisor 104 may have access to a real-time streamed or mirrored view of the XR experience 110 via a second user device (not shown). The second user device may be configured to execute a mobile companion application 105 that is programmed to display the real-time streamed or mirrored view of the XR experience 110. The mobile companion application 105 may comprise software programmed to execute the present disclosure. The second user device may be any device comprising one or more displays, such as described above. In some instances, the second user device may be any device comprising a user interactive device (e.g., buttons, touchscreen, keyboard, etc.) that allows the supervisor 104 to provide an input to the second user device. In some cases, the second user device may provide the supervisor 104 with a non-stereoscopical view of the user's 102 experience 110. For example, the mobile companion application 105 may display the experience 110 in a wider field of view than is provided to the user 102 so that the supervisor 104 can see what is to the right and left of the user's view. As an alternative, the supervisor 104 may be provided with an extended view to that of the user 102 in all angles including in the diagonal, up, and down directions. As an alternative, the mobile companion application 105 of the supervisor 104 may provide such content asynchronously, such as at a later time. The mobile companion application 105 may further provide a console 130 which allows the supervisor 104 to intervene (e.g., trigger actions or prompts) in the user's 102 virtual reality or augmented reality scene 125. Such interventions may include manipulating characters in the scene, triggering audio, visual, and/or haptic change in the XR environment, or taking administrative action such as starting a new learning module or ending the therapy session.

A control system 106 may provide content for the user's 102 virtual reality experience 110. In some instances, a third user device 108 having a user interface (e.g., GUI) may be used to design, create, update, modify, remove, and/or select the XR content of the virtual reality experience 110. For example, the third device may be used by the supervisor 104 and/or another individual or entity. The control system 106 may be hardware and/or software. In some instances, the control system 106 can reside on the third user device 108, such as as an application or a program. Alternatively, the control system 106 can reside on the first user device and/or on the second user device, such as as an application or a program. In some instances, the control system 106 may reside on a server and/or communicate via one or more computer networks with the first, second, and/or third user device. In some instances, the control system 106 may be distributed across one or more devices (e.g., server hardware, first user device, second user device, etc.) which individually, or collectively, perform the operations of the control system 106. The control system 106 can be a computer control system, as described further below. In some cases, the control system 106 may control the XR content. In some cases, the control system 106 may pair the mobile companion application of the supervisor 104 with the XR experience 110 of the user 102. For example, the mirroring of the XR experience 110, and/or the one or more commands from the console 130 to the XR experience 110 may be communicated between the first user device and the second user device through the control system 106.

Data collected about the user 102 with relation to the XR experience 110, such as from one or more sensors, may be stored and/or transmitted to the first user device, the second user device, the third user device 108, and/or the control system 106.

Figure 2:
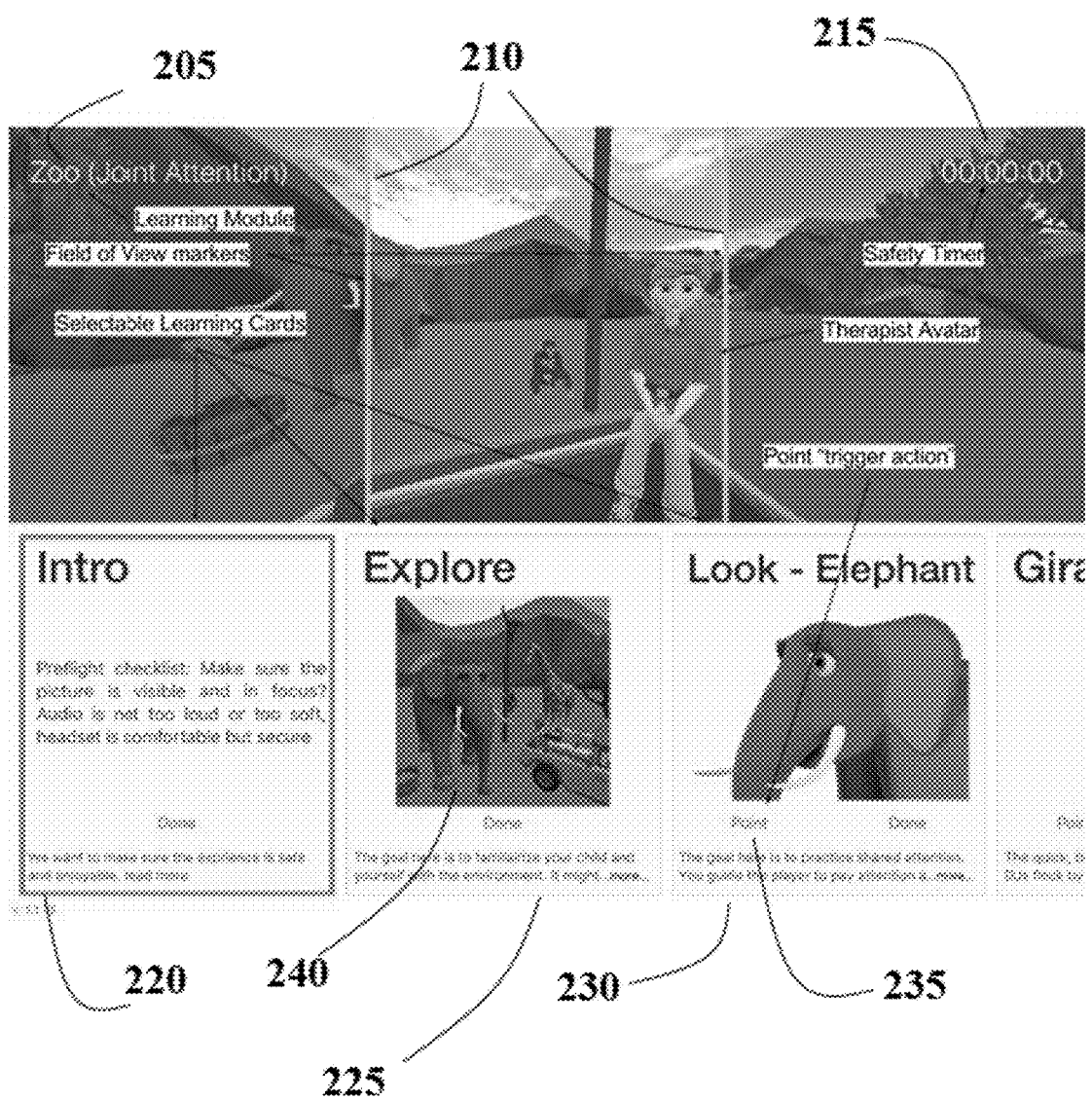
FIG. 2 shows an illustration of a mobile companion application display.

FIG. 2 shows an illustration of what a mobile companion application may display to a supervisor of a user. The mobile companion application 200 may comprise "field of view" markers 210 distinguishing the boundary between what the user is viewing and the extended view of the supervisor. These "field of view" markers 210 need not be limited to the left and right boundaries, and, in the alternative, can mark the boundaries in other directions, including the diagonal, up, or down directions. The supervisor may further be provided with a selection of learning cards 220, 225, 230 (e.g., "Intro," "Explore," "Look-Elephant," "Giraffe"), including actions 235 to trigger (e.g., "Point") and thumbnail pictures 240 of the selection of learning cards 220, 225, and 230. The companion application display may also include an indication of the learning module 205 that the user is "playing" and a display of progress checking mechanisms 215 such as a safety timer.

In one embodiment, more devices may be paired, as needed, for increased monitoring. For example, a second companion application that provides a camera view can be used as an in-room monitor. A supervisor may view the user in a XR session through a small video window on the companion application interface. For example, a user device of a user may be paired with at least about 2, 3, 4, 5, 6, 7, 8, 9, 10, 15, 20, 25, 30, 35, 40, 45, 50 or more devices of supervisors, each having their own device. Alternatively or in addition, a user device of a user may be paired with at most about 50, 45, 40, 35, 30, 25, 20, 15, 10, 9, 8, 7, 6, 5, 4, 3, or 2 devices of supervisors. In some cases, a supervisor may be paired with a plurality of users. For example, a user device of a supervisor may be paired with at least 2, 3, 4, 5, 6, 7, 8, 9, 10, 15, 20, 25, 30, 35, 40, 45, 50 or more devices of users, each having their own device. Alternatively or in addition, a user device of a supervisor may be paired with at most about 50, 45, 40, 35, 30, 25, 20, 15, 10, 9, 8, 7, 6, 5, 4, 3, or 2 devices of users. In some cases, a virtual reality experience may allow a plurality of users (e.g., peer users) to interact with each other in the virtual reality experience, such as for a group therapy session.

In one embodiment, the pairing of these devices (e.g., devices for supervisors, devices for users, etc.) may be remote which allows for teletherapy or tele-education sessions. The devices can be paired over a network, such as over the internet, intranet, and/or extranet, so that the companion application may operate remotely from the user.

In one embodiment, the system can use a gaze tracking algorithm to determine the object of focus for the user and trigger actions and prompts based on that gaze. The system may use such tracking algorithm to collect metrics and provide an analytics dashboard comprising data such as reaction time to a task, whether the user is taking fixation brakes, gaze accuracy, and how steady their gaze is on an object versus a neurotypical user. Alternatively, the system can use other algorithms and/or sensors to monitor a different type of user response. Alternatively, the system may compare the user with other users receiving the same or similar XR content. These analytics may provide not only the metrics tracked during the user's session but also a longitudinal view of the user's performance progress. See FIG. 7 for an illustration of an analytics dashboard. This dashboard may be used as a user progress report and contain information such as task category, task name, start date, total number of sessions, total number of minutes, total number of trials, total number of successes, success rate, best week, user profile data including such things as, for example, user age and gender, and a graphical illustration of the progress of the user such as, for example, user's reaction time, gaze accuracy, gaze stability, and fixation breaks. The dashboard may contain supplemental analytics on each progress category based on the goals of the training objective (e.g., Total Minutes: "Exceeds 10 minutes per session effective session duration"; Total Trials: "Meets minimum effective repetitions per session"; Success Rate: "Exceeds expected 75% success rate", Total Sessions: "18 left out of 150 Recommended Total"). The dashboard may contain other sensory data, such as measured by the one or more sensors described elsewhere herein. The sensory data can be indicative of a user's progress toward one or more goals, such as a reaction time, gaze stability, gaze accuracy, response volume, the presence or lack of a movement, the presence or lack of speaking, or other outputs by the user. The sensory data can comprise data otherwise undetectable or difficult to detect or quantify with traditional therapy methods. In some instances, the dashboard may contain other metrics such as a quiz or test score (e.g., mathematical quiz or test), physical exam score (e.g., number of successful jumping jacks, etc.).

In one embodiment, the system can integrate motion controllers into the therapy modules to track the user's motions in the virtual or augmented reality system. For instance, in a joint attention module where the user is evaluated on his or her ability to respond to pointing, there may be a lesson where the user can point in real space holding a controller. The system can then track where the gesture lands in the virtual or augmented reality space and base actions and prompts accordingly. In another instance, in a module where the user is trained for interaction with the police, the same motion tracking capability may track the hand position of the user to determine if the user is exhibiting behavior that may put them in danger with the police.

In one embodiment, the system can integrate voice recognition technology to enable therapeutic conversation training for the user in the XR space. For instance, a user may be given simple scenarios where the user answers the door and finds themselves having a back and forth conversation with a virtual character that leverages voice recognition mixed with override input from the supervisor to create a coherent training environment.

Editing XR Content

XR content may be segmented into distinct units, such as "learning modules" and "learning cards." A learning module can represent a milestone objective for the user. For example, a learning module can comprise a distinct set of therapeutic, educational, and/or training content that attempts to improve one or more target skills in the user. In some aspects, the system may comprise a collection of learning modules from which a supervisor may select to opt into to "play" with a user.

Figure 3:
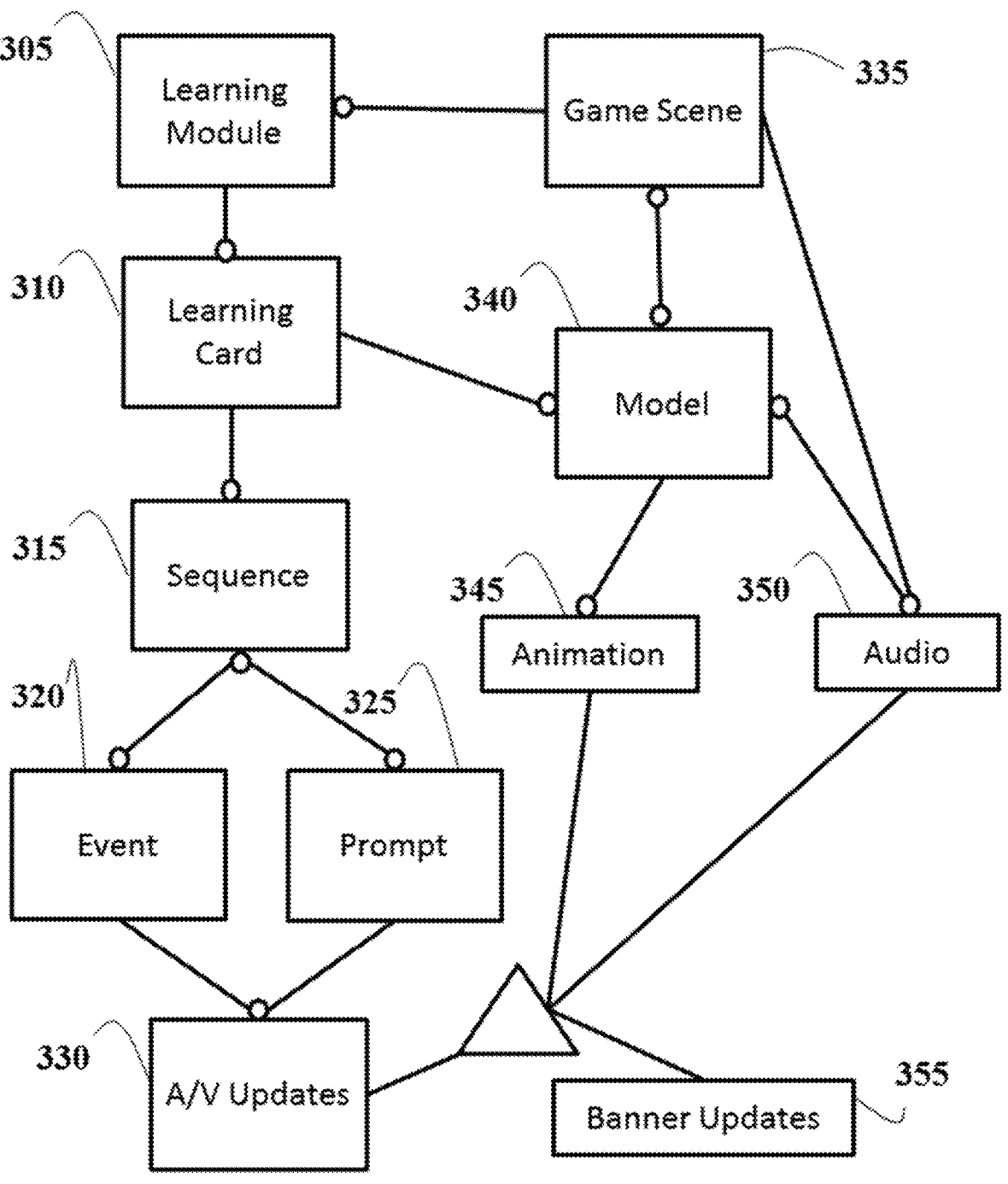
FIG. 3 shows a logical model of a learning module.

FIG. 3 depicts a logical model for a learning module 305. In FIG. 3, each line ending with a circle denotes a "one to many" relationship, in which a line connector represents "one" and a circle connector represents "many." For example, a line ending with circles on both ends will denote a "one to many" relationship in both directions. Each triangle denotes an "is a" relationship. The logical model illustrates a number of editable components, including learning modules, learning cards, sequences, events, prompts, audio/visual updates, game scenes, models, animation, audio, and banner updates. The XR content may be edited at any level of component via a graphical user interface. The editable components may be edited with respect to a timeline or other time dimension. The XR content may include one-dimensional (1-D), two-dimensional (2-D), three-dimensional (3-D), and/or four-dimensional (4-D) content. The XR content may define a 360° experience, wherein the user may view the content in 360°. The XR content may define more limited experiences (e.g., 180° experience).

In this logical model, each game scene 335 may comprise one or more learning modules 305, one or more models 340 (e.g., avatar, 2-D or 3-D animated characters), and one or more audio 350. Each learning module 305 may then comprise one or more learning cards 310. Each learning card 310 may comprise one or more models 340 and one or more sequences 315. Sequences 315, which can be triggered by user events 320 or application prompts 325, can comprise one or more events 320 as well as one or more prompts 325. Each of the events 320 and the prompts 325 may in turn comprise one or more sequences 315. That is, for example, a sequence 315 may trigger an event 320, and the event 320 may also trigger a sequence 315. Additionally, each of the event 320 and the prompt 325 may comprise one or more audio/visual updates 330 ("A/V updates"). Each A/V update 330 may comprise a banner update 355 in the supervisor's application as well as an animation 345 and audio 350 element in the game scene 335. One model 340 (e.g., an animal character) may relate to one or more game scenes 335 (e.g., zoo, train station), and comprise one or more animation 345 elements and one or more audio 350 elements. An audio 350 element may comprise one or more models 340.

As discussed briefly above, a learning module 305 can represent a developmental milestone in the form of a distinct set of therapeutic, educational, and/or training content that attempts to improve one or more target skills in the user. A supervisor may opt into a learning module 305 to "play"

with a user. Each learning module 305 may be defined by the following parameters: title (e.g., "Safari"), educational focus (e.g., joint attention), unity scene (e.g., "Safari"), thumbnail image, and a collection of learning cards 310, including an Intro Learning Card. A unity scene, or the game scene 335, may comprise the game board, including the scene background and audio 350 elements independent of the models 340 (e.g., introductory music, generic background sounds), and a collection of two or three dimensional models 340, which can include the supervisor's avatar.

A learning card 310 can be a distinct playable unit within a learning module 305 that has a set of learning objectives. That is, a learning card 310 may represent a single exercise that helps move the user toward the milestone encompassed by the learning module 305. A learning card 310 may define which of a game scene's 335 models 340 are present and include a collection of sequences 315. These sequences 315 may interact both with a supervisor's companion application, such as through banner updates 355, and with the game scene 335 and models 340, such as through the animation 345 and audio 350 elements. Each learning card 310 may be defined by the following parameters: title, thumbnail image, a collection of sequences 315, and educational description, which is a long-form content that describes the purposes of the particular learning card 310. The logical flow of a learning card 310 is discussed in further detail with the discussion of FIG. 4.

A sequence 315 may be a collection of prompts 325 and events 320 that together progresses the user through some or all of the objectives of the learning card 310. A sequence 315 may be triggered either by an event 320 (e.g., the user fixes their gaze on an animal) or by an action prompt 325 on the learning card 310 which is initiated by a supervisor (e.g., the supervisor presses a button to "Point" at a Giraffe model 340). A sequence 315 may be defined by the following parameters: the event 320 or prompt 325 that triggers the sequence 315 and the collection of events 320 and prompts 325 within the sequence 315.

An event 320 may be a user action that may be explicitly captured by the XR system for the purposes of triggering A/V updates 330 and/or updating active sequences 315 that contain the event 320. An event 320 may be defined by the following parameters: the user's triggering action (e.g., maintaining gaze on the Pig model 340 for 2 seconds), and a defined set of A/V updates 330 that execute as a post-action to the triggering action (e.g., a banner 355 status update in the supervisor's companion application reading, "User has gazed at Pig," or the Pig model 340 initiating an audio 350 element such as "Oink" in the game scene 335).

A prompt 325 may be a supervisor-initiated component of a sequence 315. It may be defined by the following parameters: a named action which appears as a button for the learning card 310 (e.g., a "Point" button), clear logic for a user to complete the prompt 325, a collection of A/V updates 330 should the user fail to follow the given prompt 325 which may include a banner 355 status update to the supervisor (e.g., "Tell the user to look at the Pig if they are not picking up the visual pointing cue" displayed to the supervisor in a companion application) or an animation 345 or audio 350 update in the game scene 335 (e.g., Pig model 340 is animated 345 and/or makes a sound 350), a collection of A/V updates 330 should the user succeed in following the given prompt 325 which may include a banner 355 status update to the supervisor (e.g., "Congratulate user for looking at the Pig Model" displayed to the supervisor in a companion application) or an animation 345 or audio 350 update in the game scene 335 (e.g., Pig model 340 is animated 345 or an audio 350 is initiated for celebratory music).

An A/V update 330 may be in the form of updates to the supervisor through a banner update 355, the triggering of animation 345 or audio 350 of the models 340 in the game scene 335, or the triggering of audio 350 in the game scene 335 level independent of the models 340. For example, an A/V update 330 may be defined by the following parameter: which of banner 355, animation 345, or audio 350 is to be updated (e.g., in the case of a banner update 355, the text should be specified).

Figure 4:
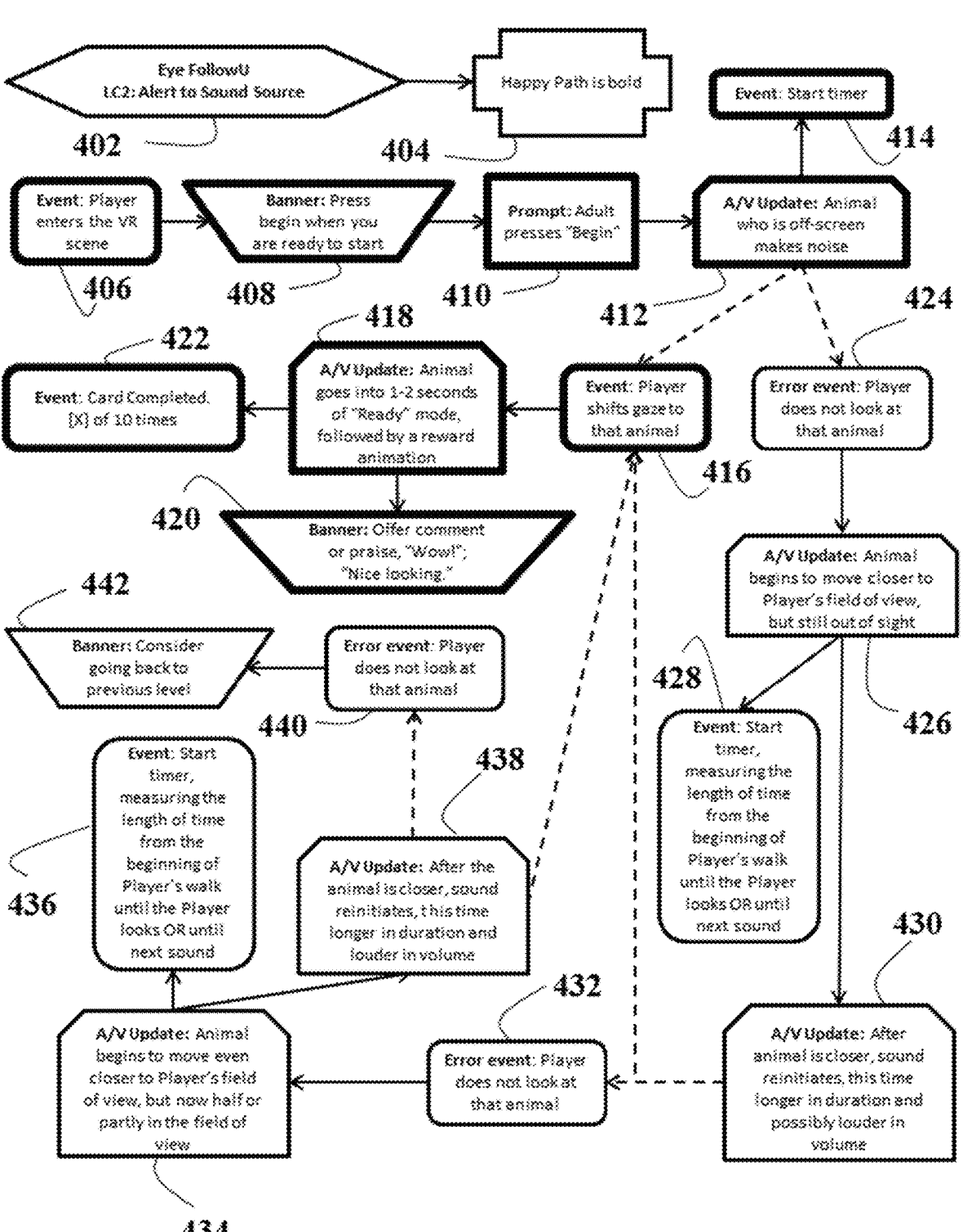
FIG. 4 shows a logical model of a learning card.

FIG. 4 shows a logical model for an illustrative learning card, element 310 in FIG. 3, titled "Eye FollowU—LC 2: Alert to Sound Source" 402. The "Eye FollowU" learning card 402 is illustrative of the logical components and methods introduced in FIG. 3 and discloses but one design of many possible. "Eye FollowU" 402 is a Card whose educational focus is joint attention. The skill within joint attention is alerting to a sound source. The player profile for the Card 402, that is, the type of affected individual for which the Card 402 is intended, is an individual who does not readily respond to the sound in his or her environment and likely has difficulty responding when his or her name is called. The behavioral goal for the Card 402 is for the user to shift his or her gaze to look at an animal model, element 340 in FIG. 3, that has produced a sound and hold the gaze on that animal for at least 2 seconds. The Card 402 may be completed when the user demonstrates this behavior at least 5 times. The Card may have the following parameters: Unity Scene (Safari); Models (Elephant, Gorilla, Adult Avatar); Thumbnail Image (figure with hand cupping ear); Sequence ([Animal] [makes appropriate animal sound]).

In an example, the Card 402 may separately provide the following notes and instructions to the supervisor in the companion application:

"This Card is for teaching the player to alert to the sound of the animal, a skill which he or she will need as he progresses through the Learning Cards. This is not intended as a 'directions following' game. So, don't tell the player to look for an animal. Let the program do the work and then join in the fun."

"LISTEN for the animal sound. WAIT for the player to find the animal. THEN, respond, offering clues only if necessary."

"Feel free to give verbal praise or comments after the Player looks at the animal."

"If the player is having trouble identifying the animal that goes with the sound, try going back to the exploratory level."

FIG. 4 illustrates the possible logical flow paths of this Learning Card 402 in action. In FIG. 4, each solid black arrow represents a definite sequence and each broken arrow represents one of many sequential options that are available.

In the logical design of the Learning Card 402, producers of the Card, such as the developers or designers, may highlight a "Happy Path" 404. The Path 404 may highlight (e.g., bold, color) the expected sequential path of a successful user, that is, a user who successfully completes the learning objective task given by the learning card. For the "Eye FollowU" Card 402, the execution sequence 406-422 is bolded as the Happy Path 404. Such highlighting may be made visible only within the system's internal design process, such as to developers or designers of the Card 402, for reference and design purposes.

The Card's 402 first event 406 occurs when the user enters the XR scene. Upon the occurrence of this event 406, the supervisor receives a banner update 408 on the companion application reading, "Press 'Begin' when you are ready to start." The supervisor initiates a prompt 410 when the supervisor presses the "Begin" button on his companion application. Upon initiation of the prompt 410, there is an A/V update 412 in the XR scene, and an animal model that is off-screen makes a noise. Simultaneously, the A/V update 412 starts a timer 414 to collect metrics on the user. After hearing the animal noise, the user may proceed with one of two events, the first event 416 in which the user successfully shifts his or her gaze to the noise-making animal model, and the second event 424 in which the user fails to look at the animal model. The user's success 416 in shifting his or her gaze initiates an A/V update 418 in which the supervisor receives a banner update 420 reading, "Offer comment or praise: 'Wow!'; 'Nice looking,'" and in the game scene the animal model goes into 1 to 2 seconds of "Ready" mode, followed by a reward animation 418. An example of an animal model in "Ready" mode 418 may be a three-dimensional elephant model jumping on all fours for 2 seconds. After the reward animation, the Card is marked completed "[x] of 10 times," 422 and the same message is displayed in the supervisor's companion application in a banner update. Alternatively, in other designs, the Card can be marked completed only after a user has completed the task a [y] number of times. If, on the other hand, the user fails to look at the animal model that made the noise 424, another A/V update 426 is initiated where the animal model begins to move closer to the user's field of view, but still remains out of sight. This update 426 triggers another program event 428 which starts a new timer that measures the duration of time from the beginning of the user's walk to either the time the user looks at the animal model or the time the animal model makes the next sound. After the animal model moves closer, in another A/V update 430, the sound reinitiates, this time longer in duration and possibly louder in volume. At this point, again, the user can proceed with one of two events, the first event 416 in which the user successfully shifts gaze to the noise-making animal model, and the second event 432 in which the user fails for a second time. The user's success will trigger the same sequence of A/V updates and events 416-422 as when the user succeeded on gazing at the first instance of the noise. If the user fails, another A/V update 434 is triggered, and the animal model is made to move even closer to the user's field of view, but now half or partly in the field of view of the user. After the animal model has moved partly within the view of the user, in another A/V update 438, the sound reinitiates, in longer duration and louder volume than the second instance of the noise. Another timer starts 436 measuring the duration of time from the beginning of the user's walk until either the user shifts his or her gaze on the animal model or the animal model makes the next sound. At this point, again, the user may proceed with one of two events, the first event 416 in which the user successfully shifts gaze to the noise-making animal model, and the second event 440 in which the user fails for the third time. The user's success will trigger the same sequence of A/V updates and events 416-422 as when the user succeeded on gazing at the first instance of the noise. This time, however, the user's failure will trigger a banner update 442 in the supervisor's companion application that reads "Consider going back to the previous level." From this logical model, the system can collect a number of data points including the number of times a user alerts to the sound source, which animal models the user responds to, the time it takes the user to alert to the sound source, and a ratio between the number of times the user had the opportunity to react to the sound to the number of times the user actually reacted. Such data may be presented to a supervisor as a progress report of the dashboard format illustrated in FIG. 7 or, alternatively, as any other format or report.

In other designs, the number of iterations, or attempts given to the user, for a certain learning exercise may be modified as needed and depending on the difficulty level of the particular learning card or learning module.

In some aspects, the system may provide teaching modules which teach functional skills using stories. These teaching modules can include placing a user in a practice environment for both routine and non-routine tasks. Beneficially, such stories provide an effective and entertaining solution to teach users how to navigate everyday interactions by placing the users in a controlled virtual or augmented reality environment, thereby shielding the users from potential actual harms and retaining control to effectively guide the users at a flexible pace.

Figure 5:
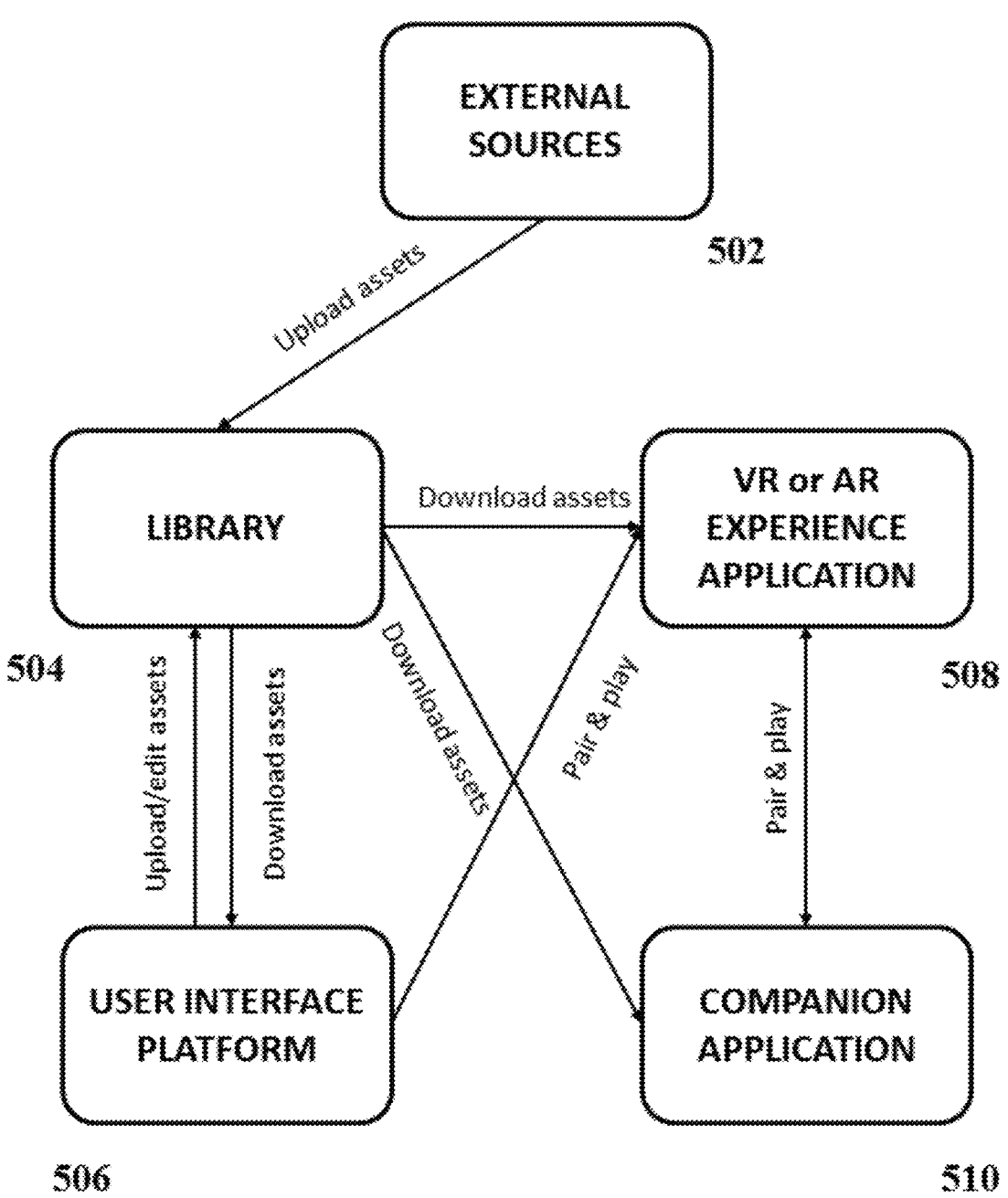
FIG. 5 illustrates a process flow for editing XR content of the present disclosure.

FIG. 5 illustrates a process flow for editing XR content of the present disclosure. A user interface platform 506 may comprise a set of tools and technologies to create, update, modify, remove, and/or select a XR experience. The user interface platform 506 may comprise a graphical user interface comprising one or more user interactive objects (e.g., buttons, sliders, etc.). For example, the user interface platform 506 may be a web-based interface. Alternatively, the user interface platform 506 may be a non-web based interface. The user interface platform 506 may allow a user to manipulate one or more editable components, such as the learning card or learning module described elsewhere herein. For example, the user interface platform 506 may be used to create, modify, or otherwise edit a network or graph of interactions between the editable components. The editable components may be edited with respect to a timeline or other time dimension.

An editable component may include any component of the XR content, such as learning modules, learning cards, sequences, events, prompts, audio/visual updates, game scenes, models (e.g., avatars), animation, audio (e.g., dialogue files, sound effect files, etc.), and banner updates. An editable component may be edited by editing an asset and/or a state of the component. An asset can be any media or data that can be used in the XR content. An asset may be internally created within the user interface platform 506. Alternatively an asset may be sourced from an external source 502. For example, an asset may include, be associated with, and/or be defined by a model file (e.g., defining meshes, bones, animations, textures, etc.), an audio file, a video file, an image file, animation controller files, mesh files, animation files, html (e.g., for documents and guides, etc.) prefabs (e.g., object template files), and other data. In some instances, a combination of assets may be bundled as an asset package. The asset package may be compressed and stored as single files. A state may describe a particular instance of an asset, such as an animation character. An asset may have a plurality of states with different transitions (or a set of transitions) associated between the different plurality of states. For example, a state type can include an animation, audio, banner, conditional, delay, dialogue, fixation check, inverse kinematics, monitor user interface update, randomization, reward bell generator, shuffler, teleport, variable counter, variable flipper, variable setter, vehicle, and other elements. An editable component, asset, and/or state may have a plurality of versions.

Using the user interface platform 506, a user may create, edit, or remove any editable component. For example, a user may create a new learning card. A user may modify the collection and/or order of learning cards in a learning module. A user may edit or copy (e.g., duplicate) an existing learning card from a library 504. A user may localize an existing learning card, such as to swap out different assets and/or states (e.g., dialogue or audio files, banner text, environment, animation meshes). A user may add, modify, or remove one or more assets in the learning card. A user may change or upgrade the version of one or more assets, change or upgrade the version of one or more states, and/or change or upgrade one or more learning cards. A user may pair the platform 506 with a XR experience application 508 to play, monitor, or supervise the XR content on the XR experience application 508. A user may publish XR content to the library 504. For example, the user may publish a XR experience template, publish individual editable components such as leaning cards, and/or publish individual assets (or asset packages) or individual states to the library 504. Beneficially, other users may access the library 504 to download the XR content to select or customize their own XR experiences. The XR content created or modified by the user may be published for further development and/or for production (e.g., by the XR experience application 508). In some instances, a user may also gather metrics for a set of states.

The library 504 may be accessed to download one or more components for editing and/or execution. For example, as described earlier, the user interface platform 506 may download one or more assets, states, or learning cards, or other editable components from the library 504, such as for use in creation, modification, and/or updates to a XR experience, or for pairing with and execution on the XR experience application 508. In another example, the XR experience application may directly access the library 504 to download one or more components, such as a learning card, to execute a XR experience for a XR user. In another example, a companion application 510 may access the library 504 to download one or more components, such as a learning card, to execute, supervise, and/or monitor a XR experience in the XR experience application 508 (e.g., after pairing with the XR experience application).

Figure 6A:
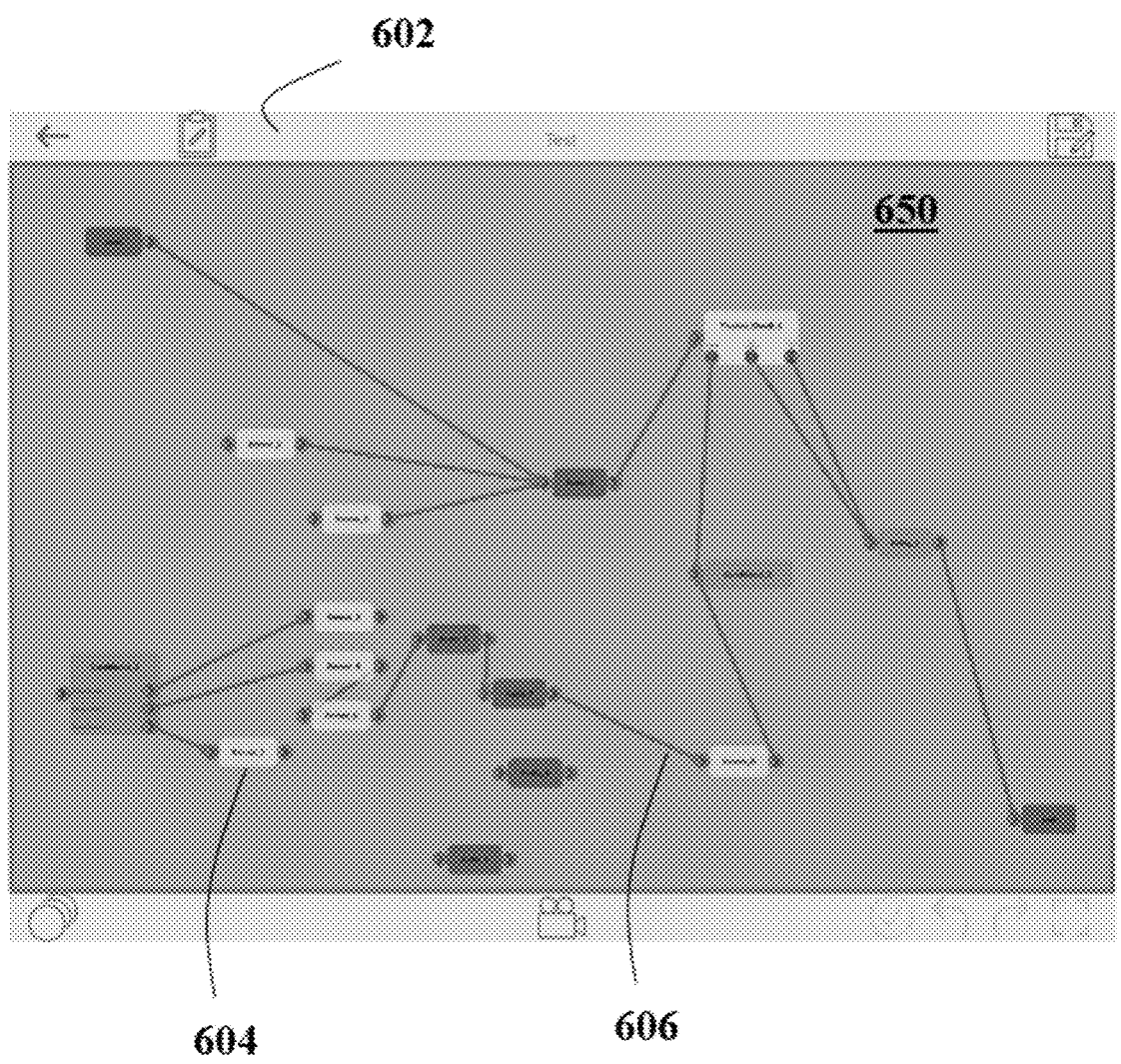
FIGS. 6A-6B illustrate a user interface platform for editing XR content.
Figure 6B:
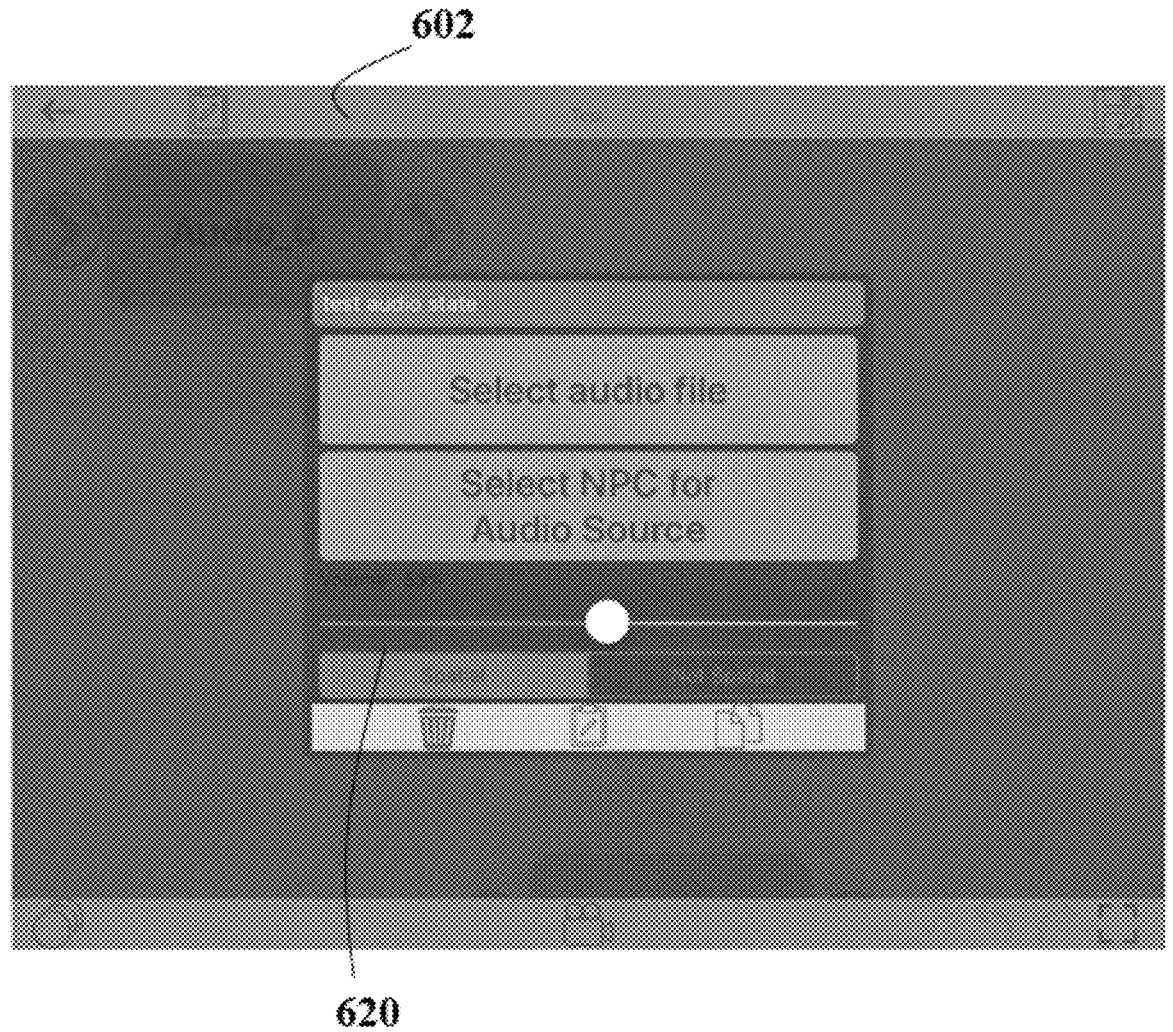

FIGS. 6A-6B illustrate a user interface platform for editing XR content. FIG. 6A illustrates a user interface 602 comprising a canvas for creating or editing a state machine (e.g., finite state machine). The state machine may define the set of states, such as by defining each of the states and transitions between each of the different states. The state machine may define the set of states for all assets in the learning card. The state machine may be validated for orphan states, dead ends, infinite loops, and unconnected connectors. The canvas may illustrate a network or graph of nodes 604 and connectors 606 between the nodes to define the set of states to define the XR experience. For example, the network or graph of nodes and connectors may represent the different sequences of logical flow paths in the XR experience. A node may comprise a state type of an asset in the virtual or augmented reality experience, and a connector between two nodes can define a chronological sequence between the two nodes in the virtual or augmented reality content. The state type represented by the node in the canvas may not necessarily present itself during the actual AR or VR experience. For example, a conditional node may branch off via three different connectors to three different nodes (e.g., banner events, audio files, etc.). In the XR experience, depending on the condition satisfied (or dissatisfied) by the user, the user may be presented with only one of the three different sequential nodes (e.g., banner events, audio files, etc.). The user interface platform may be used to define the states for all possible conditions and account for all possible logical flow paths (e.g., such as the flow paths illustrated in the learning card example of FIG. 4). FIG. 6B illustrates a user interface platform with a control module. The platform may present a control module 620 for editing a state, such as an audio state. The control module 620 may be presented or triggered to present (e.g., display to the user) when the node (e.g., state) to be edited is selected. For example, the control module 620 may allow the user to select the specific audio file (e.g., from the library 504 in FIG. 5), select the model for the audio source, select a volume of the audio, and/or select between a spatial or non-spatial audio option. The control module 620 may present different editing options for different types of states (e.g., banner event can allow selection of font, size, color, animation effect, etc.).

The platform may facilitate collaborative authoring and editing of XR content. In some instances, a plurality of users may, together, create and/or edit XR content. For example, a first user may create at least a first portion of XR content and publish, save, and/or distribute the first portion of XR content on the platform (e.g., in a library), and a second user may edit the first portion of XR content and/or add other portions of XR content to the existing XR content, and publish, save, and/or distribute such modifications on the platform to complete or modify an XR module (e.g., learning card, learning module, etc.). Any number of users may contribute to a single unit of XR content, such as about 2, 3, 4, 5, 6, 7, 8, 9, 10, 20, 30, 40, 50, 100 or more users. In some instances, a creator or author of XR content may control the number of users or identify of users with permissions to modify the XR content. In some instances, a user may be granted permission, such as by the creator or by another user, to modify the XR content. In other instances, any user may have permission to modify the XR content. Such permissions may be associated with the XR content (e.g., as metadata). Different users may have different permissions to execute different actions on particular XR content, such as reading, modifying, playback, testing, reviewing or evaluating, troubleshooting (e.g., debugging), publishing, distributing, and the like.

In some instances, the platform may have one or more pre-publication or pre-distribution tests for the XR content before publication or distribution. For example, there may be a clinical efficacy test, a safety test, a publication rights test, a technical test, and the like. In such cases, a particular XR content may be published or distributed only upon passing the one or more tests. In some cases, a particular XR content may be published or distributed to a desired user base only upon passing the one or more tests. For example, if an XR content fails a first test, it may still be distributed to a targeted user or group of users, but not allowed to be distributed to the public. In some instances, a test may have a binary passing or failing evaluation. In some instances, a test may be scored, wherein there may or may not be a passing score. In such cases, the test score may be associated with the XR content after publication—the score may be viewable to one or more users or to the public, or alternatively, the score may be viewable upon request, or alternatively, the score may not be viewable. In some instances, a test may be automatically performed by one or more algorithms programmed to perform the tests. In some instances, a test may require submission of one or more evidence documents (e.g., a clinician's approval, regulatory approval, peer review, etc.). In some instances, a test may require voluntary statements (e.g., that a user has publication rights and has no knowledge of infringement of others' rights). In some instances, a test may be performed by other users of the platform, such as for beta testing to pass a technical test before publication to a wider user base.

In some aspects, provided are systems and methods for profiling a user. For example, the user may be diagnosed with a condition, such as a neurodevelopmental or learning disorder. In some cases, data collected (or recorded) for one or more users may be aggregated to build behavior models for one or more conditions (e.g., mental or developmental disorders). Such behavior models can be leveraged as diagnostic tools for users to be evaluated through the XR system. For example, a plurality of behavior models for different mental or developmental disorders can be stored in a library of behavior models, such as in one or more databases. A plurality of behavior models for each XR environment, scene, or experience may be stored in a library of behavior models, such as in one or more databases. A behavior model for a first type of developmental disorder can comprise data exhibited by one or more users known to suffer from the first type of developmental disorder when placed in a first XR environment. When a user to be diagnosed is placed in the same first XR environment, or an environment similar to the first XR environment, the data collected on the user may be compared to the behavior model for the first type of developmental disorder to determine whether the user has the first type of developmental disorder or not, and/or determine a degree to which the user suffers from the first type of developmental disorder. In some instances, the data collected for the user to be diagnosed may be compared to a plurality of behavior models to determine which one or more conditions the user may suffer from (and to what degree). By way of example, the higher the % similarity between the collected data for the user and the data stored for the behavior model, the more likely it is (and with higher degree) that the user suffers from the condition of the behavior model. In some instances, a user being diagnosed may be placed in a plurality of different XR environments, scenes, and/or experiences (e.g., sensory calming modules, teaching modules, learning modules, etc.) and an overall performance by the user may be compared to the library of behavior models. Such comparisons may be made individually by XR environments (for each type of condition) and/or by condition (for each type of XR environments), and then aggregated (e.g., average, mean, median, other statistical computation or evaluation). Beneficially, the XR systems may accurately and precisely diagnose a user with a condition based on comparisons of accurately measured empirical data (for example, compared to general guidelines or hunches that a child is not attentive enough), and determine a degree of intensity or progression of a condition. This may be particularly beneficial for diagnosing and treating mental or developmental disorders where it is difficult to quantify symptoms. In some instances, the diagnosis of the XR systems may be implemented by one or more computer algorithms, such as machine learning algorithms, which are trained with increasing data input (e.g., more users, more therapy sessions using the XR systems, etc.). For example, the accuracy of the diagnosis may increase as the iterations increases.

Beneficially, the platforms, systems, and methods of the present disclosure may be used to flexibly customize a XR experience for a profiled or diagnosed user. For example, a particular XR experience may be prescribed or recommended to a user based on the user profile. In another example, an existing XR experience may be customized for the user based on the user profile. In another example, an entirely new XR experience may be created for the user based on the user profile. A XR experience may be published and shared in a commonly accessible library to prevent duplication of effort. In some instances, the prescription, recommendation, and/or customization can be performed by human experts. Alternatively or in addition, they may be prescribed by the system via one or more computer algorithms (e.g., machine learning algorithms). In some cases, the diagnosis, prescription, or recommendation may be made without human input. The accuracy of the diagnosis, prescription, or recommendation may increase with increasing iterations. In some instances, the virtual or augmented reality experiences and therapies can be tailored to the needs of individual users either manually by the human expert (e.g., therapist) or using computer algorithms. For example, the tailoring can be performed based at least on prior conditions defined in the user profile and/or based on data collected throughout the user's and others' use of the XR system.

Control Systems

Figure 8:
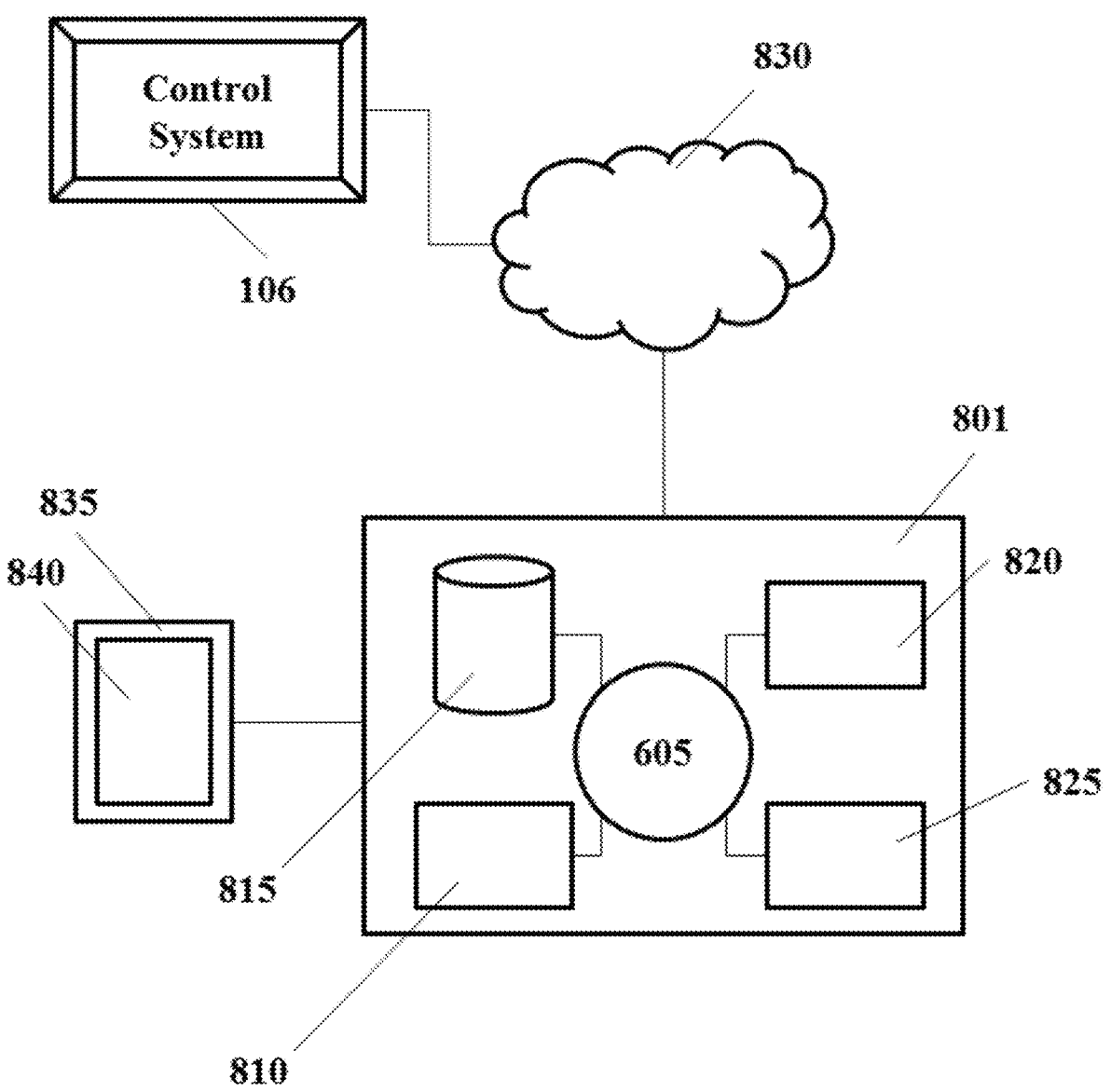
FIG. 8 shows a computer control system that is programmed or otherwise configured to implement methods provided herein.

The present disclosure provides computer control systems that are programmed to implement methods of the disclosure. FIG. 8 shows a computer system 801 that is programmed or otherwise configured to operate and display a user interface to edit virtual reality or augmented reality content, execute a XR environment with or without the use of supplemental headsets or gear, execute algorithms within the virtual reality or augmented reality platform or a companion application to the virtual reality or augmented reality platform, track, save, and analyze a user's behaviors and responses in a XR environment, and/or execute and pair a companion application that may allow a supervising user to monitor and control in real-time a user's virtual reality or augmented reality experience on a second, third, or nth display screen. The computer system 801 can be an electronic device of a user or a computer system that is remotely located with respect to the electronic device. The electronic device can be a mobile electronic device. The computer system 801 may be used to treat a neurodevelopmental disorder, such as, for example, autism. The computer system 801 may communicate with the control system 106 of FIG. 1. In some cases, the control system 106 may comprise the computer system 801.

The computer system 801 includes a central processing unit (CPU, also "processor" and "computer processor" herein) 805, which can be a single core or multi core processor, or a plurality of processors for parallel processing. The computer system 801 also includes memory or memory location 810 (e.g., random-access memory, read-only memory, flash memory), electronic storage unit 815 (e.g., hard disk), communication interface 820 (e.g., network adapter) for communicating with one or more other systems, and peripheral devices 825, such as cache, other memory, data storage and/or electronic display adapters. The memory 810, storage unit 815, interface 820 and peripheral devices 825 are in communication with the CPU 805 through a communication bus (solid lines), such as a motherboard. The storage unit 815 can be a data storage unit (or data repository) for storing data. The computer system 801 can be operatively coupled to a computer network ("network") 830 with the aid of the communication interface 820. The network 830 can be the Internet, an internet and/or extranet, or an intranet and/or extranet that is in communication with the Internet. The network 830 in some cases is a telecommunication and/or data network. The network 830 can include one or more computer servers, which can enable distributed computing, such as cloud computing. The network 830, in some cases with the aid of the computer system 801, can implement a peer-to-peer network, which may enable devices coupled to the computer system 801 to behave as a client or a server.

The CPU 805 can execute a sequence of machine-readable instructions, which can be embodied in a program or software. The instructions may be stored in a memory location, such as the memory 810. The instructions can be directed to the CPU 805, which can subsequently program or otherwise configure the CPU 805 to implement methods of the present disclosure. Examples of operations performed by the CPU 805 can include fetch, decode, execute, and writeback.

The CPU 805 can be part of a circuit, such as an integrated circuit. One or more other components of the system 801 can be included in the circuit. In some cases, the circuit is an application specific integrated circuit (ASIC).

The storage unit 815 can store files, such as drivers, libraries and saved programs. The storage unit 815 can store user data, e.g., user preferences and user programs. The computer system 801 in some cases can include one or more additional data storage units that are external to the computer system 801, such as located on a remote server that is in communication with the computer system 801 through an intranet or the Internet.

The computer system 801 can communicate with one or more remote computer systems through the network 830. For instance, the computer system 801 can communicate with a remote computer system of a user (e.g., XR user, supervisor, therapist). Examples of remote computer systems include personal computers (e.g., portable PC), slate or tablet PC's (e.g., Apple® iPad, Samsung® Galaxy Tab), telephones, Smart phones (e.g., Apple® iphone, Android-enabled device, Blackberry®), or personal digital assistants. The user can access the computer system 801 via the network 830.

Methods as described herein can be implemented by way of machine (e.g., computer processor) executable code stored on an electronic storage location of the computer system 801, such as, for example, on the memory 810 or electronic storage unit 815. The machine executable or machine readable code can be provided in the form of software. During use, the code can be executed by the processor 805. In some cases, the code can be retrieved from the storage unit 815 and stored on the memory 810 for ready access by the processor 805. In some situations, the electronic storage unit 815 can be precluded, and machine-executable instructions are stored on memory 810.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 801, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 801 can include or be in communication with an electronic display 835 that comprises a user interface (UI) 840 for providing, for example an editing platform for editing XR content, and/or displaying images or videos used to simulate an augmented or virtual reality experience to the user. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 805.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention.

Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A system for treating or supplementing the treatment of a subject with one or more mental or developmental conditions, comprising: a processor of a computing device; and a non-transitory medium with instructions stored thereon that, when executed by the processor, direct the computing device to perform operations comprising:
   a. generating a subject profile, wherein the subject profile is based at least in part on one or more characteristics of the subject;
   b. assigning one or more therapeutic goals to the subject, wherein the one or more therapeutic goals are based at least in part on the subject profile; and
   c. presenting a virtual world to the subject using a virtual or augmented reality device that provides visual, auditory, or haptic stimulation, wherein the virtual world comprises interactive content configured to aid the subject in progressing towards the one or more therapeutic goals.

2. The system of claim 1, wherein the one or more therapeutic goals are related to a symptom of the one or more mental or developmental conditions of the subject.

3. The system of claim 2, wherein the one or more mental or developmental conditions comprise autism.

4. The system of claim 2, wherein the one or more mental or developmental conditions comprise ADHD.

5. The system of claim 1, wherein the one or more characteristics of the subject comprise one or more cognitive or perceptual conditions.

6. The method of claim 5, wherein the one or more cognitive or perceptual conditions comprise one or more phobias.

7. The method of claim 5, wherein the one or more cognitive or perceptual conditions comprise one or more dysmorphias.

8. The system of claim 1, wherein the one or more characteristics of the subject comprise the gender of the subject.

9. The system of claim 1, wherein the one or more characteristics of the subject comprise the educational level of the subject.

10. The system of claim 1, wherein the one or more characteristics of the subject comprise the exposure level of the subject to XR therapies.

11. The system of claim 1, wherein the one or more characteristics of the subject comprise the age of the subject.

12. The system of claim 1, wherein generating the subject profile comprises selecting a pre-existing profile from a library of profiles.

13. The system of claim 1, wherein the virtual world presented to the subject comprises a selection from a pre-existing library of virtual worlds.

14. The system of claim 13, wherein the selection is based at least in part on the subject profile.

15. The system of claim 14, wherein the virtual world is generated based at least in part on the subject profile.

16. The system of claim 13, wherein the selection is based at least in part on the one or more therapeutic goals.

17. The system of claim 1, wherein the virtual world presented to the subject is first generated by the system.

18. The system of claim 1, wherein the one or more therapeutic goals comprise learning or training a certain social skill, increasing concentration ability, training processing speed, facilitation communication, reducing anxiety, promoting self-esteem, learning functional skills, or managing sensory overload, or any combination thereof.

19. The system of claim 1, wherein generating the subject profile further comprises comparing the one or more characteristics of the subject with a database.

20. The system of claim 1, wherein the interactive content is configured to aid in learning or training a social skill.

21. A system for treating or supplementing the treatment of a subject with one or more mental or developmental conditions, comprising: a processor of a computing device; and a non-transitory medium with instructions stored thereon that, when executed by the processor, direct the computing device to perform operations comprising:
   a. presenting a subject with a virtual world using a virtual or augmented reality device that provides visual, auditory, or haptic stimulation, wherein the virtual world comprises interactive content configured to aid the subject in progressing towards one or more therapeutic goals;
   b. measuring the subject's progress towards the one or more therapeutic goals;
   c. generating a subject profile, wherein the profile is based on the progress of the subject towards one or more therapeutic goals; and
   d. modifying the virtual world based at least in part on the subject profile.

22. The system of claim 21, wherein the one or more therapeutic goals are related to a symptom of the one or more mental or developmental conditions of the subject.

23. The system of claim 22, wherein the one or more mental or developmental conditions comprise autism.

24. The system of claim 22, wherein the one or more mental or developmental conditions comprise ADHD.

25. The system of claim 22, wherein the one or more therapeutic goals comprise learning or training a certain social skill, increasing concentration ability, training processing speed, facilitation communication, reducing anxiety, promoting self-esteem, learning functional skills, or managing sensory overload, or any combination thereof.

26. The system of claim 21, wherein the interactive content is configured to aid in learning or training a social skill.

* * * * *